United States Patent
Unger

US005705187A

[11] Patent Number: 5,705,187
[45] Date of Patent: Jan. 6, 1998

[54] COMPOSITIONS OF LIPIDS AND STABILIZING MATERIALS

[75] Inventor: Evan C. Unger, Tucson, Ariz.

[73] Assignee: ImaRx Pharmaceutical Corp., Tucson, Ariz.

[21] Appl. No.: 417,238

[22] Filed: Apr. 5, 1995

Related U.S. Application Data

[63] Continuation-in-part of Ser. No. 307,305, Sep. 16, 1994, and Ser. No. 160,232, Nov. 30, 1993, Pat. No. 5,542,935, which is a continuation-in-part of Ser. No. 159,674, Nov. 30, 1993, abandoned, which is a continuation-in-part of Ser. No. 76,250, Jun. 11, 1993, Pat. No. 5,580,575, which is a continuation-in-part of Ser. No. 717,084, Jun. 18, 1991, Pat. No. 5,228,446, and Ser. No. 716,899, Jun. 18, 1991, abandoned, each is a continuation-in-part of Ser. No. 569,828, Aug. 20, 1990, Pat. No. 5,088,499, which is a continuation-in-part of Ser. No. 455,707, Dec. 22, 1989, abandoned, said Ser. No. 307,305, is a continuation-in-part of Ser. No. 159,687, Nov. 30, 1993, Pat. No. 5,585,112, which is a continuation-in-part of Ser. No. 160,232, Nov. 30, 1993, Pat. No. 5,542,935, which is a continuation-in-part of Ser. No. 76,239, Jun. 11, 1993, Pat. No. 5,469,854, which is a continuation-in-part of Ser. No. 717,084, and Ser. No. 716,899, each is a continuation-in-part of Ser. No. 569,828, which is a continuation-in-part of Ser. No. 455,707.

[51] Int. Cl.$^6$ .................................................. A61K 9/127
[52] U.S. Cl. .................. 424/450; 424/9.321; 424/9.4; 424/43; 424/45; 428/402.2
[58] Field of Search .................. 424/450, 9.321, 424/9.4, 43, 45; 428/402.2; 436/829

[56] References Cited

U.S. PATENT DOCUMENTS

| | | | |
|---|---|---|---|
| 3,532,500 | 10/1970 | Priest et al. | 96/91 |
| 3,873,564 | 3/1975 | Schneider et al. | 260/309.6 |
| 4,089,801 | 5/1978 | Schneider | 252/316 |
| 4,162,282 | 7/1979 | Fulwyler et al. | 264/9 |
| 4,192,859 | 3/1980 | Mackaness et al. | 424/5 |
| 4,224,179 | 9/1980 | Schneider | 252/316 |
| 4,276,885 | 7/1981 | Tickner et al. | 128/660 |
| 4,310,505 | 1/1982 | Baldeschwieler et al. | 424/1 |
| 4,310,506 | 1/1982 | Baldeschwieler et al. | 424/1 |
| 4,315,514 | 2/1982 | Drewes et al. | 128/653 |
| 4,331,654 | 5/1982 | Morris | 424/38 |
| 4,344,929 | 8/1982 | Bonsen et al. | 424/15 |
| 4,426,330 | 1/1984 | Sears | 260/403 |
| 4,428,924 | 1/1984 | Millington | 424/4 |
| 4,442,843 | 4/1984 | Rasor et al. | 128/660 |
| 4,466,442 | 8/1984 | Hilmann et al. | 128/653 |
| 4,533,254 | 8/1985 | Cook et al. | 366/176 |
| 4,534,899 | 8/1985 | Sears | 260/403 |
| 4,544,545 | 10/1985 | Ryan et al. | 424/1.1 |
| 4,569,836 | 2/1986 | Gordon . | |
| 4,572,203 | 2/1986 | Feinstein | 128/661 |
| 4,586,512 | 5/1986 | Do-huu et al. | 128/660 |
| 4,603,044 | 7/1986 | Geho et al. | 424/9 |
| 4,615,879 | 10/1986 | Runge et al. | 424/9 |
| 4,620,546 | 11/1986 | Aida et al. | 128/660 |
| 4,636,381 | 1/1987 | Takada | 424/38 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,718,433 | 1/1988 | Feinstein | 128/660 |
| 4,728,575 | 3/1988 | Gamble et al. | 428/402.2 |
| 4,728,578 | 3/1988 | Higgins et al. | 428/462 |
| 4,731,239 | 3/1988 | Gordon | 424/9 |
| 4,737,323 | 4/1988 | Martin et al. | 264/4.3 |
| 4,774,958 | 10/1988 | Feinstein | 128/660.01 |
| 4,775,522 | 10/1988 | Clark, Jr. | 424/9 |
| 4,776,991 | 10/1988 | Farmer et al. | 264/4.3 |
| 4,781,871 | 11/1988 | West, III et al. | 264/4.3 |
| 4,790,891 | 12/1988 | Halliday et al. | 149/2 |
| 4,830,858 | 5/1989 | Payne et al. | 424/450 |
| 4,844,882 | 7/1989 | Widder et al. | 424/9 |
| 4,863,717 | 9/1989 | Keana | 424/9 |
| 4,865,836 | 9/1989 | Long, Jr. | 424/5 |
| 4,877,561 | 10/1989 | Iga et al. | 264/4.3 |
| 4,893,624 | 1/1990 | Lele | 128/399 |
| 4,895,719 | 1/1990 | Radhakrishnan | 424/45 |
| 4,898,734 | 2/1990 | Mathiowitz et al. | 424/426 |
| 4,900,540 | 2/1990 | Ryan | 424/9 |
| 4,921,706 | 5/1990 | Roberts et al. | 424/450 |
| 4,927,623 | 5/1990 | Long, Jr. | 424/5 |
| 4,938,947 | 7/1990 | Nicolau et al. | 424/1.1 |
| 4,957,656 | 9/1990 | Cerny et al. | 252/311 |
| 4,981,692 | 1/1991 | Popescu et al. | 424/422 |
| 4,987,154 | 1/1991 | Long, Jr. | 514/772 |
| 4,996,041 | 2/1991 | Arai et al. | 424/9 |
| 4,997,819 | 3/1991 | Yamaguchi | 514/54 |
| 5,000,960 | 3/1991 | Wallach | 424/450 |
| 5,008,050 | 4/1991 | Cullis et al. | 264/4.3 |

(List continued on next page.)

FOREIGN PATENT DOCUMENTS

| | | |
|---|---|---|
| 0 107 559 | 5/1984 | European Pat. Off. . |
| 0077752 B1 | 3/1986 | European Pat. Off. . |

(List continued on next page.)

OTHER PUBLICATIONS

Weiner: Drug Development & Industrial Pharmacy 15(10) pp. 1523–1554 (1989).

Miller, D.L., "Ultrasonic Detection of Resonant Cavitation Bubbles in a Flow Tube by Their Second–Harmonic Emissions", *Ultrasonics* Sep. 1981, pp. 217–224.

(List continued on next page.)

*Primary Examiner*—Gollamudi S. Kishore
*Attorney, Agent, or Firm*—Woodcock Washburn Kurtz Mackiewicz & Norris LLP

[57] ABSTRACT

Compositions comprising, in an aqueous carrier, a lipid and a material which is capable of stabilizing the composition. The stabilizing material is associated non-covalently with said lipid and is present in an amount sufficient to coat the lipid but insufficient to raise the viscosity of the composition. The compositions are particularly suitable for use in diagnostic applications, including ultrasound. The compositions can take the form of vesicular compositions, such as micelles and liposomes.

220 Claims, No Drawings

U.S. PATENT DOCUMENTS

| | | | |
|---|---|---|---|
| 5,013,556 | 5/1991 | Woodle | 424/450 |
| 5,045,304 | 9/1991 | Schneider et al. | 424/9 |
| 5,049,388 | 9/1991 | Knight et al. | 424/450 |
| 5,088,499 | 2/1992 | Unger | 128/662.2 |
| 5,091,188 | 2/1992 | Haynes | 424/450 |
| 5,114,703 | 5/1992 | Wolf et al. | 424/5 |
| 5,123,414 | 6/1992 | Unger | 128/654 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |
| 5,149,319 | 9/1992 | Unger | 604/22 |
| 5,171,755 | 12/1992 | Kaufman | 514/759 |
| 5,186,922 | 2/1993 | Shell et al. | 128/654 |
| 5,190,982 | 3/1993 | Erbel et al. | 521/56 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9 |
| 5,198,225 | 3/1993 | Meybeck et al. | 424/450 |
| 5,205,287 | 4/1993 | Erbel et al. | 128/632 |
| 5,209,720 | 5/1993 | Unger | 604/22 |
| 5,213,804 | 5/1993 | Martin et al. | 424/450 |
| 5,215,680 | 6/1993 | D'Arrigo | 252/307 |
| 5,219,538 | 6/1993 | Henderson et al. | 428/402.2 |
| 5,228,446 | 7/1993 | Unger et al. | 128/662.02 |
| 5,230,882 | 7/1993 | Unger | 424/9 |
| 5,246,707 | 9/1993 | Haynes | 424/450 |
| 5,271,928 | 12/1993 | Schneider | 424/9 |
| 5,305,757 | 4/1994 | Unger et al. | 128/662.02 |
| 5,310,540 | 5/1994 | Giddey et al. | 424/9 |
| 5,315,997 | 5/1994 | Widder et al. | 128/653.3 |
| 5,316,771 | 5/1994 | Barenholz et al. | 424/450 |
| 5,334,381 | 8/1994 | Unger | 424/9 |
| 5,344,930 | 9/1994 | Riess et al. | 544/84 |
| 5,350,571 | 9/1994 | Kaufman et al. | 424/9 |
| 5,352,435 | 10/1994 | Unger | 424/9 |
| 5,380,519 | 1/1995 | Schneider et al. | 424/9 |
| 5,393,524 | 2/1995 | Quay | 424/9 |
| 5,409,688 | 4/1995 | Quay | 424/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.51 |
| 5,469,854 | 11/1995 | Unger et al. | 128/662.02 |
| 5,470,582 | 11/1995 | Supersaxo et al. | 424/489 |
| 5,487,390 | 1/1996 | Cohen et al. | 128/662.02 |
| 5,496,535 | 3/1996 | Kirkland | 424/9.37 |
| 5,505,932 | 4/1996 | Grinstaff et al. | 424/9.3 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| 5,560,364 | 10/1996 | Porter | 128/662.02 |
| 5,562,893 | 10/1996 | Lohrmann | 424/9.52 |
| B1 4,229,360 | 11/1991 | Schneider et al. | 260/403 |

FOREIGN PATENT DOCUMENTS

| | | |
|---|---|---|
| 0 243 947 | 4/1987 | European Pat. Off. . |
| 0 231 091 | 8/1987 | European Pat. Off. . |
| 0231091 | 8/1987 | European Pat. Off. . |
| 0 272 091 | 6/1988 | European Pat. Off. . |
| 0 320 433 A2 | 12/1988 | European Pat. Off. . |
| 0 324 938 | 7/1989 | European Pat. Off. . |
| 0 338 971 | 10/1989 | European Pat. Off. . |
| 357163 A1 | 3/1990 | European Pat. Off. . |
| 0 361 894 | 4/1990 | European Pat. Off. . |
| 0 216 730 | 1/1991 | European Pat. Off. . |
| 0 467 031 A2 | 5/1991 | European Pat. Off. . |
| 441468 A2 | 8/1991 | European Pat. Off. . |
| 0 357 164 B1 | 10/1991 | European Pat. Off. . |
| 0 458 745 A1 | 11/1991 | European Pat. Off. . |
| 0 314 764 B1 | 9/1992 | European Pat. Off. . |
| 0 554 213 A1 | 8/1993 | European Pat. Off. . |
| 0 727 225 A2 | 8/1996 | European Pat. Off. . |
| 032329 | 9/1981 | Japan . |
| 63-60943 | 3/1988 | Japan . |
| 2193095 | 2/1988 | United Kingdom . |
| 80/02365 | 11/1980 | WIPO . |
| 82/10642 | 5/1982 | WIPO . |
| 85/01161 | 3/1985 | WIPO . |
| 86/00238 | 1/1986 | WIPO . |
| 86/01103 | 2/1986 | WIPO . |
| 89/05040 | 6/1989 | WIPO . |
| 4004384 | 5/1990 | WIPO . |
| 90/04384 | 5/1990 | WIPO . |
| 90/04943 | 5/1990 | WIPO . |
| 91/00086 | 1/1991 | WIPO . |
| 91/12823 | 9/1991 | WIPO . |
| 91/15244 | 10/1991 | WIPO . |
| 92/10166 | 6/1992 | WIPO . |
| 92/17212 | 10/1992 | WIPO . |
| 92/17213 | 10/1992 | WIPO . |
| 92/17436 | 10/1992 | WIPO . |
| 92/21382 | 12/1992 | WIPO . |
| 93/05819 | 1/1993 | WIPO . |
| 93/06869 | 4/1993 | WIPO . |
| 93/13809 | 7/1993 | WIPO . |
| 93/17718 | 9/1993 | WIPO . |
| 93/20802 | 10/1993 | WIPO . |
| 94/09829 | 5/1994 | WIPO . |
| 94/16739 | 8/1994 | WIPO . |
| 94/21302 | 9/1994 | WIPO . |
| 95/06518 | 3/1995 | WIPO . |
| 95/07072 | 3/1995 | WIPO . |
| 96/04018 | 2/1996 | WIPO . |
| 96/09793 | 4/1996 | WIPO . |

OTHER PUBLICATIONS

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1974).

Thanassi, "Aminomalonic Acid: Spontaneous Decarboxylation and Reaction with 5–Deoxypyridoxal", *Biochemistry*, vol. 9, No. 3, pp. 525–532 (1970).

Stelmashok et al., *Koordinatsionnaya Khimiya*, vol. 3, No. 4, pp. 524–527 (1977) (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812: 55–65 (1985).

Mayer et al., "Vesicles of Variable Size Produced by a Rapid Extrusion Procedure", *Biochimica et Biophysica Acta*, vol. 858, pp. 161–168 (1986).

Cheng, et al., "The Production and Evaluation of Contrast–Carrying Liposomes Made with an Automatic High Pressure System", *Investigative Radiology*, vol. 22, pp. 47–55 (1987).

Jain, et al., *Introduction to Biological Membranes*, Ch. 9, pp.192–231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultrasound Contrast Material", *Radiology*, vol. 145, pp. 759–762 (1982).

Keller et al., "Successful Left Ventricular Opacitication Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocardiography, I: In Vitro Development and Quantitative Analysis of Echo Contrast Agents", *JACC*, vol. 3, No. 1, pp. 14–20 (1984).

Ten Cate et al., "Two–Dimensional Contrast Echocardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772g (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophases of Dipalmitoyl Phosphatidylcholines", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp. 70–80 (1989).

Mann et al., "Formation of Iron Oxides in Unilamellar Vesicles", *Journal of Colloid and Interface Science*, vol. 122, No. 2, pp. 326–335 (1988).

Anderson et al., "Manganese (III) Complexes in Oxidative Decarboxylation of Acids", *J. Am. Chem. Soc.*, vol. 92, No. 8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman D., "Physiochemical Properties of Phospholipids and Lipid Water Systems", *Liposome Technology*, Gregoriadis, G., ed., vol.1, pp. 1–19 (CRC Press, Boca Raton, FL 1984).

Violante et al., "Particulate Suspensions as Ultrasonic Contrast Agents for Liver and Spleen", *Inv. Rad.*, vol. 23, pp. S924–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, *Experience*, Sonicator™, Heat Systems—Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.*, vol. 108, pp. 2321–2327 (1986).

Regen, "Polymerized Vesicles", *J. Am. Chem. Soc.*, vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC)*, vol. 44(3), pp. 322–326 (1981) (abstract).

J. Vion–Dury et al., *J. Pharmacol. Exper. Ther.*, vol. 250(3), pp. 1113–1118 (1989) (abstract).

M.R. Zalutsky et al., *Invest. Radiol.*, vol. 22(2), pp. 141–147 (1987) (abstract).

Crowe et al., *Archives of Biochemistry and Biophysics*, vol. 242, pp. 240–247 (1985).

Crowe et al., *Archives of Biochemistry and Biophysics*, vol. 220, pp. 477–484 (1983).

Dorland's Illustrated Medical Dictionary, p. 946, 27th ed. (W.B. Saunders Company, Philadelphia 1988).

*Liposome Technology*, Gregoriadis, G., ed., vol. I, pp. 1–18, 29–35, 51–65 and 79–107 (CRC Press Inc., Boca Raton, FL, (1984).

Madden et al., *Chemistry and Physics of Lipids*, vol. 53, pp. 37–46 (1990).

Sinkula et al., *J. Pharm. Sci.*, vol. 64, pp. 181–210 (1975).

Shiina et al., "Hyperthermiaby Low–frequency Synthesized Ultrasound", *IEEE Engineering*, pp. 879–880, vol. 2 (abstract).

McAvoy et al., *IEEE Engineering, Ultrasonics Symposium Proceedings*, vol. 2, pp. 677–1248 (abstract).

Chapman et al., "Biomembrane Phase Transitions", *J. Biol. Chem.*, 1974, 249:2512–2521.

Hug et al., "Liposomes for the Transformation of Eukaryotic Cells", *Biochimica et Biophysica Acta*, 1991, 1097:1–17.

Marsh, CRC Handbook of Lipid Bilayers (CRC Press, Boca Raton, FL 1990) pp. 139–141.

Szoka et al., "Procedure for Preparation of Liposomes With Large Internal Aqueous Space . . . ", *Proc. Natl. Acad. Sci.* 1978, 75:4194–4198.

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.*, 1965, 13:238–252.

Carson et al., *Ultrasound in Med. & Biol.* 3, 1978, 341–350.

Chiellini et al., *Polymers in Medicine II: Biomedical and Pharmaceutical Applications*, (Plenum Press, New York and London) pp. 387–396.

deGier et al., "Relations Between Liposomes and Biomembranes", *Annals of the New York Academy of Sciences*, 1978, 308:85–99.

Felgner et al., "Lipofection: A highly efficient, lipid–mediated DNA–transfection procedure", *Proc. Natl. Acad. Sci.*, 1987, 84:7413–7417.

Gabizon et al., "Liposome formulations with prolonged circulation time in blood and enhanced uptake by tumors", *Proc. Natl. Acad. Sci.*, 1988, 85:6949–6953.

Garelli, et al., *Biochimica et Biophysica Acta*, vol. 1127:41–48 (1992).

Kawai et al., "New Procedure for DNA Transfection with Polycation and Dimethyl Sulfoxide", *Molecular and Cellular Biology*, 1984, 4:1172–1174.

Kuo et al., "Metallocene Antitumor Agents. Solution and Solid–State Molybdenocene Coordination . . . ", *J. Am. Chem. Soc.*, 1991, 113:9027–9045.

*Mammalian Cell Biotechnology: A Practical Approach*, M. Butler, 1991 (Oxford University Press, New York), pp. 57–70.

Mathiowitz et al., "Photochemical Rupture of Microcapsules: A Model System", *Journal of Applied Polymer Science*, 1981, 26:809–822.

May et al., "Cationic Liposomes Enable Bovine Herpesvirus Type 2 DNA to Infect Cells", *Acta virol.*, 1991, 35:107.

Poznansky et al., "Biologica Approaches to the Controlled Delivery of Drugs: A Critical Review", *Pharmacol, Rev.*, 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature*, 1992, 359:67–70.

Thompson, Larry, "At Age 2, Gene Therapy Enters a Growth Phase", *Science* 1992, 258:744–746.

Trubetskoy et al. "Cationic liposomes enhance targeted delivery and expression of exogenous DNA . . . ", Biochimica et Biophysica Acta, 1992, 131:311–313.

Umemura et al., "Studies on Sonodynamic Cancer Therapy", *IEEE*, 1992, O–7803–0785, pp. 354–355.

Williams, "Human Gene Therapy: Searching for Better Vectors", *ASM News* [American Society for Microbology] 1992, 58:67–69.

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release* 1992, 19:269–274.

Mathiowitz et al., "Polyanhydride Microspheres as Drug Carriers", *Journal of Applied Polymer Science*, vol. 35, pp. 755–774 (1988).

Sankaram et al., "Cholesterol–Induced Fluid–Phase Immiscibility in Membranes", *Proc. Natl. Acad. Sci.*, vol. 88, pp. 8686–8690 (1991).

*Scientific Apparatus Catalog 92/93* (VWR Scientific 1991), "Syringes", pp. 1511–1513: Filtration, Syringe Filters, pp. 766–768; Filtration, Membranes, pp. 750–753; Filtration, Filter Holders, p. 744.

Gramiak et al., *Radiology*, "Detection of Intracardiac Blood Flow by Pulsed Echo–Ranging", pp. 415–418 (1971).

Feigenbaum et al., *Circulation*, "Identification of Ultrasound Echoes from the Left Ventricle by Use of Intracardiac Injections of Indocyanine Green", vol. XL1, pp. 615–621 (1970).

Santaella, et al., *FEBS* 13463, "Extended In Vivo Blood Circulation Time of Fluorinated Liposomes", vol. 336, No. 3, pp. 481–484 (1993).

Kost, et al, *Polymers in Medicine II*, "Ultrasonic Modulated Drug Delivery Systems", pp.387–396.

Brown and Langer, *Annual Review Medicine*, 1988, 39:221 29, Annual Review, Inc., "Transdermal Delivery of Drugs", pp. 221–229.

Moseley, et al., *Microbubbles: A Novel MR Susceptibility Contrast Agent*, abstract, 1991 Napa, California Meeting of the Society for Magnetic Resonance in Medicine.

Ter–Pogossian, Physical Principles and Instrumentation, "Computed Body Tomography", Chapter 1, pp. 1–7.

Aronberg, Techniques, "Computed Body Tomography", Chapter 2, pp. 9–36.

Canfield, L. et al., "Incorporation of β–Carotene into Mixed Micelles", *Methods in Enzymology* 1990, 189, 418–422.

El–Gorab, M. and Underwood, "Solubilizatioin of β–Carotene and Retinol into Aqueous Solutions of Mixed Micelles", *Biochimica et Biophysica Acta*, 306, 58–66.

Shinoda, K. et al., "Colloidal Surfactants; Some Physiochemical Properties", Chapter 1, pp. 1–96, Academic Press, New York, 1963.

Sutherland, G.R. et al., "Color Doppler Myocardial Imaging: A New Technique for the Assessment of Myocardial Functions", *J. of the Am. Soc. of Echocardiography* 1994, 7(5), 441–458.

Uhlendorf, V., "Physics of Ultrasound Contrast Imaging: Scattering in the Linear Range", *IEEE Transactions on Ultrasonics, Ferroelectrics and Frequency Control* 1994, 40(1), 70–79.

Dittrich, "Cardiac Muscle Ischemia and Infarction", *The Second Annual International Symposium on Contrast Agents in Diagnostic Ultrasound*, Atlantic City, NJ (May 7, 1996) (abstract).

Pantely, "Intravenous Contrast Echocardiography–Tissue Imaging & Quantification of Coronary Blood Flow", *The Second Annual International Symposium on Contrast Agents in Diagnostic Ultrasound*, Atlantic City, NJ (May 7, 1996) (abstract).

Schutt et al., "Osmotically Stabilized Microbubble Sonographic Contrast Agents", *Acad. Radiol.*, vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta*, 1192, pp. 61–70 (1994).

Frézard, et al., "Fluorinated Phospholipid–Based Vesicles as Potential Drug Carriers: Encapsulation/Sustaining of Drugs and Stability in Human Serum", *Art, Cells, Blood Subs., and Immob. Biotech.*, 22(4), pp. 1403–1408 (1994).

Weiner, N. et al., "Liposomes As a Drug Delivery System", *Drug Development and Industrial Pharmacy* 1989, 15(10), 1523–1554.

COMPOSITIONS OF LIPIDS AND STABILIZING MATERIALS

CROSS REFERENCE TO RELATED APPLICATIONS

This application is a continuation-in-part of U.S. application Ser. No. 307,305, filed Sep. 16, 1994 now pending, which is a continuation-in-part of U.S. application Ser. No. 159,687, filed Nov. 30, 1993 now U.S. Pat. No. 5,585,112, which is a continuation-in-part of U.S. application Ser. No. 160,232, filed Nov. 30, 1993 now U.S. Pat. No. 5,542,935, issued Aug. 6, 1996, which is a continuation-in-part of U.S. application Ser. No. 076,239, filed Jun. 11, 1993 now U.S. Pat. No. 5,469,854, issued Nov. 28, 1995, which is a continuation-in-part of U.S. application Serial No. 717,084, now U.S. Patent No. 5,228,446, issued Jul. 20, 1993 and U.S. application Serial No. 716,899, now abandoned, both of which were filed Jun. 18, 1991 and which are continuations-in-part of U.S. application Ser. No. 569,828, filed Aug. 20, 1990, now U.S. Pat. No. 5,088,499, issued Feb. 18, 1992, which is a continuation-in-part of U.S. application Ser. No. 455,707, filed Dec. 22, 1989, now abandoned.

This application is also a continuation-in-part of U.S. application Ser. No. 160,232, filed Nov. 30, 1993 now U.S. Pat. No. 5,542,935, issued Aug. 6, 1996, which is a continuation-in-part of U.S. application Ser. No. 159,674, filed Nov. 30, 1993, now abandoned, which is a C-I-P of U.S. application Ser. No. 076,250, filed Jun. 11, 1993, now U.S. Pat. No. 5,580,575, which is a continuation-in-part of U.S. application Ser. No. 717,084, now U.S. Pat. No. 5,228,446, issued Jul. 20, 1993 and U.S. application Ser. No. 716,899, now abandoned, both of which were filed Jun. 18, 1991 and which are continuations-in-part of U.S. application Ser. No. 569,828, filed Aug. 20, 1990, now U.S. Pat. No. 5,088,499, issued Feb. 18, 1992, which is a continuation-in-part of U.S. application Ser. No. 455,707, filed Dec. 22, 1989, now abandoned.

FIELD OF THE INVENTION

The present invention relates to novel compositions of lipids and stabilizing materials and the use thereof. More particularly, the present invention relates to novel compositions of lipids and stabilizing materials and their use in the administration of biologically active agents.

BACKGROUND OF THE INVENTION

Ultrasound is a valuable diagnostic imaging technique for studying various areas of the body, for example, the vasculature, including tissue microvasculature. Ultrasound provides certain advantages over other diagnostic techniques. For example, diagnostic techniques involving nuclear medicine and X-rays generally results in exposure of the patient to ionizing electron radiation. Such radiation can cause damage to subcellular material, including deoxyribonucleic acid (DNA), ribonucleic acid (RNA) and proteins. Ultrasound does not involve such potentially damaging radiation. In addition, ultrasound is relatively inexpensive relative to other diagnostic techniques, including computed tomography (CT) and magnetic resonance imaging (MRI), which require elaborate and expensive equipment.

Ultrasound involves the exposure of a patient to sound waves. Generally, the sound waves dissipate due to absorption by body tissue, penetrate through the tissue or reflect off of the tissue. The reflection of sound waves off of tissue, generally referred to as backscatter or reflectivity, forms the basis for developing an ultrasound image. In this connection, sound waves reflect differentially from different body tissues. This differential reflection is due to various factors, including the constituents and the density of the particular tissue being observed. Ultrasound involves the detection of the differentially reflected waves, generally with a transducer that can detect sound waves having a frequency of one megahertz (MHz) to ten MHz. The detected waves can be integrated into an image which is quantitated and the quantitated waves converted into an image of the tissue being studied.

Ultrasound imaging techniques generally also involve the use of contrast agents. Contrast agents are used to improve the quality and usefulness of images which are obtained via ultrasound. Exemplary contrast agents include, for example, suspensions of solid particles, emulsified liquid droplets, and gas-filled bubbles. See, e.g., Hilmann et al., U.S. Pat. No. 4,466,442, and published International Patent Applications WO 92/17212 and WO 92/21382.

The quality of images produced from ultrasound has improved significantly. Nevertheless, further improvement is needed, particularly with respect to images involving vasculature in tissues that are perfused with a vascular blood supply. Accordingly, there is a need for improved ultrasound techniques, including improved contrast agents which are capable of providing medically useful images of the vasculature and vascular-related organs.

The reflection of sound from a liquid-gas interface is extremely efficient. Accordingly, bubbles, including gas-filled bubbles, are useful as contrast agents. The term "bubbles", as used herein, refers to vesicles which are generally characterized by the presence of one or more membranes or walls surrounding an internal void that is filled with a gas or precursor thereto. Exemplary bubbles include, for example, liposomes, micelles and the like. As discussed more fully hereinafter, the effectiveness of bubbles as contrast agents depends upon various factors, including, for example, the size and/or elasticity of the bubble.

With respect to the effect of bubble size, the following discussion is provided. As known to the skilled artisan, the signal which is reflected off of a bubble is a function of the radius ($r^6$) of the bubble (Rayleigh Scatterer). Thus, a bubble having a diameter of 4 micrometer (μm) possesses about 64 times the scattering ability of a bubble having a diameter of 2 μm. Thus, generally speaking, the larger the bubble, the greater the reflected signal.

However, bubble size is limited by the diameter of capillaries through which the bubbles must pass. Generally, contrast agents which comprise bubbles having a diameter of greater than 10 μm can be dangerous since microvessels may be occluded. Accordingly, it is desired that greater than about 99% of the bubbles in a contrast agent have a diameter of less than 10 μm. Mean bubble diameter is important also, and should be greater than 1 μm, with greater than 2 μm being preferred. The volume weighted mean diameter of the bubbles should be about 7 to 10 micrometer.

As noted above, the elasticity of bubbles is also important. This is because highly elastic bubbles can deform, as necessary, to "squeeze" through capillaries. This decreases the likelihood of occlusion. The effectiveness of a contrast agent which comprises bubbles is also dependent on the bubble concentration. Generally, the higher the bubble concentration, the greater the reflectivity of the contrast agent.

Another important characteristic which is related to the effectiveness of bubbles as contrast agents is bubble stability. As used herein, particularly with reference to gas-filled bubbles, "bubble stability" refers to the ability of bubbles to retain gas entrapped therein after exposure to a pressure greater than atmospheric pressure. To be effective as contrast agents, bubbles generally need to retain greater than 50% of entrapped gas after exposure to pressure of 300 millimeters (mm) of mercury (Hg) for about one minute. Particularly effective bubbles retain 75% of the entrapped gas after being exposed for one minute to a pressure of 300 mm Hg, with an entrapped gas content of 90% providing especially effective contrast agents. It is also highly desirable that, after release of the pressure, the bubbles return to their original size. This is referred to generally as "bubble resilience."

Bubbles which lack desirable stability provide poor contrast agents. If, for example, bubbles release the gas entrapped therein in vivo, reflectivity is diminished. Similarly, the size of bubbles which possess poor resilience will be decreased in vivo, also resulting in diminished reflectivity.

The stability of bubbles disclosed in the prior art is generally inadequate for use as contrast agents. For example, the prior art discloses bubbles, including gas-filled liposomes, which comprise lipoidal walls or membranes. See, e.g., Ryan et al., U.S. Pat. Nos. 4,900,540 and 4,544,545; Tickner et al., U.S. Pat. No. 4,276,885; Klaveness et al., WO 93/13809 and Schneider et al., EPO 0 554 213 and WO 91/15244. The stability of the bubbles disclosed in the aforementioned references is poor in that as the solutions in which the bubbles are suspended become diluted, for example, in vivo, the walls or membranes of the bubbles are thinned. This results in a greater likelihood of rupture.

Various studies have been conducted in an attempt to improve bubble stability. Such studies have included, for example, the preparation of bubbles in which the membranes or walls thereof comprise materials that are apparently strengthened via crosslinking. See, e.g., Klaveness et al., WO 92/17212, in which there are disclosed bubbles which comprise proteins crosslinked with biodegradable crosslinking agents. Alternatively, bubble membranes can comprise compounds which are not proteins but which are crosslinked also with biocompatible compounds. See, e.g., Klaveness et al., WO 92/17436, WO 93/17718 and WO 92/21382.

Prior art techniques for stabilizing bubbles, including crosslinking, suffer from various drawbacks. For example, the crosslinking described above generally involves the use of new materials, including crosslinked proteins or other compounds, for which the metabolic fate is unknown. In addition, crosslinking requires additional chemical process steps, including isolation and purification of the crosslinked compounds. Moreover, crosslinking imparts rigidity to the membranes or walls of the bubbles. This results in bubbles having reduced elasticity and, therefore, a decreased ability to deform and pass through capillaries. Thus, there is a greater likelihood of occlusion of vessels with prior art contrast agents that are stabilized via crosslinking.

Accordingly, new and/or better stabilized contrast agents and methods for providing same are needed. The present invention is directed to this, as well as other, important ends.

SUMMARY OF THE INVENTION

The present invention is directed to stabilized lipid compositions. Specifically, in one aspect, the present invention relates to a lipid composition comprising, in a aqueous carrier, a lipid and a material which is capable of stabilizing the composition. The stabilizing material is associated non-covalently with the lipid and is present in the composition in an amount sufficient to coat the lipid but insufficient to raise the viscosity of the composition. The lipid composition may further comprise, as desired, gas and/or gaseous precursors. Also, if desired, the lipid composition may additionally comprise bioactive agents.

Another aspect of the invention relates to a vesicular composition comprising, in an aqueous carrier, vesicles comprising a lipid, and a material which is capable of stabilizing the composition. The stabilizing material is associated non-covalently with the lipid and is present in the composition in an amount sufficient to coat the lipid but insufficient to raise the viscosity of the composition. The vesicular composition may further comprise, as desired, gas and/or gaseous precursors. Also, if desired, the vesicular composition may further comprise bioactive agents.

Yet another aspect of the invention relates to a formulation for diagnostic or therapeutic use. The formulations comprise, in combination with a bioactive agent, a lipid and a material which is capable of stabilizing the composition. The stabilizing material is associated non-covalently with the lipid and is present in an amount sufficient to coat the lipid but insufficient to raise the viscosity of the composition. The formulation may further comprise, as desired, gas and/or gaseous precursors.

Still another aspect of the invention relates to a process for the preparation of a stabilized lipid composition. The process comprises combining together a lipid and a stabilizing material which is capable of associating non-covalently with the lipid. The stabilizing material is combined with the lipid in an amount sufficient to coat the lipid but insufficient to raise the viscosity of the composition.

Another aspect of the present invention relates to a process for the preparation of a formulation for diagnostic or therapeutic use. The process comprises combining together a bioactive agent and a composition which comprises a lipid and a stabilizing material which is associated non-covalently with the lipid. The stabilizing material is present in the composition in an amount sufficient to coat the lipid but insufficient to raise the viscosity of the composition.

Yet another aspect of the invention relates to a stabilized lipid composition that is prepared by combining together a lipid and a stabilizing material which is capable of associating non-covalently with the lipid. The stabilizing material is combined with the lipid in an amount sufficient to coat the lipid but insufficient to raise the viscosity of the composition.

Another aspect of the invention relates to a stabilized formulation for diagnostic or therapeutic use. The formulation is prepared by combining together a bioactive agent and a composition which comprises a lipid and a material which is capable of stabilizing the formulation. The stabilizing material is associated non-covalently with the lipid and is present in an amount sufficient to coat the lipid but insufficient to raise the viscosity of the formulation.

Yet another aspect of the invention relates to a method for providing an image of an internal region of a patient. The method comprises (i) administering to the patient a lipid composition comprising, in an aqueous carrier, a lipid, a gas or a gaseous precursor and a material which is capable of stabilizing the composition, wherein the stabilizing material is associated non-covalently with the lipid and is present in an amount sufficient to coat the lipid but insufficient to raise the viscosity of the composition; and (ii) scanning the patient using ultrasound to obtain a visible image of the region.

Still another aspect of the invention relates also to a method for providing an image of an internal region of a patient. The method comprises (i) administering to the patient a vesicular composition comprising, in an aqueous carrier, vesicles comprising a lipid, a gas or a gaseous precursor and a material which is capable of stabilizing the composition, wherein the stabilizing material is associated non-covalently with the lipid and is present in an amount sufficient to coat the lipid but insufficient to raise the viscosity of the composition; and (ii) scanning the patient using ultrasound to obtain a visible image of the region.

Yet another aspect of the invention relates to a method for diagnosing the presence of diseased tissue in a patient. The method comprises (i) administering to the patient a lipid composition comprising, in an aqueous carrier, a lipid, a gas or a gaseous precursor and a material which is capable of stabilizing the composition, wherein the stabilizing material is associated non-covalently with the lipid and is present in an amount sufficient to coat the lipid but insufficient to raise the viscosity of the composition; and (ii) scanning the patient using ultrasound to obtain a visible image of any diseased tissue in the patient.

Another aspect of the invention relates also to a method for diagnosing the presence of diseased tissue in a patient. The method comprises (i) administering to the patient a vesicular composition comprising, in an aqueous carrier, vesicles comprising a lipid, a gas or a gaseous precursor and a material which is capable of stabilizing the composition, wherein the stabilizing material is associated non-covalently with the lipid and is present in an amount sufficient to coat the lipid but insufficient to raise the viscosity of the composition; and (ii) scanning the patient using ultrasound to obtain a visible image of any diseased tissue in the patient.

Also encompassed by the present invention is a method for the therapeutic delivery in vivo of a bioactive agent. The method comprises administering to a patient a therapeutically effective amount of a formulation which comprises, in combination with a bioactive agent, a lipid composition which comprises a lipid and a material which stabilizes the composition. The stabilizing material is associated non-covalently with the lipid and is present in the composition in an amount sufficient to coat the lipid but insufficient to raise the viscosity of the composition.

These and other aspects of the invention will become more apparent from the present specification and claims.

DETAILED DESCRIPTION OF THE INVENTION

As employed above and throughout the disclosure, the following terms, unless otherwise indicated, shall be understood to have the following meanings.

"Lipid" refers to a synthetic or naturally-occurring amphipathic compound which comprises a hydrophilic component and a hydrophobic component. Lipids include, for example, fatty acids, neutral fats, phosphatides, glycolipids, aliphatic alcohols and waxes, terpenes and steroids.

"Lipid composition" refers to a composition which comprises a lipid compound. Exemplary lipid compositions include suspensions, emulsions and vesicular compositions.

"Lipid formulation" refers to a composition which comprises a lipid compound and a bioactive agent.

"Vesicle" refers to a spherical entity which is characterized by the presence of an internal void. Preferred vesicles are formulated from lipids, including the various lipids described herein. In any given vesicle, the lipids may be in the form of a monolayer or bilayer, and the mono- or bilayer lipids may be used to form one or more mono- or bilayers. In the case of more than one mono- or bilayer, the mono- or bilayers are generally concentric. The lipid vesicles described herein include such entities commonly referred to as liposomes, micelles, bubbles, microbubbles, microspheres and the like. Thus, the lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The internal void of the vesicles may be filled with a liquid, including, for example, an aqueous liquid, a gas, a gaseous precursor, and/or a solid or solute material, including, for example, a bioactive agent, as desired.

"Vesicular composition" refers to a composition which is formulated from lipids and which comprises vesicles.

"Vesicle formulation" refers to a composition which comprises vesicles and a bioactive agent.

"Liposome" refers to a generally spherical cluster or aggregate of amphipathic compounds, including lipid compounds, typically in the form of one or more concentric layers, for example, bilayers. They may also be referred to herein as lipid vesicles.

"Patient" refers to animals, including mammals, preferably humans.

"Bioactive agent" refers to a substance which is used in connection with an application that is therapeutic or diagnostic in nature, such as in methods for diagnosing the presence or absence of a disease in a patient and/or in methods for the treatment of disease in a patient. As used herein, "bioactive agent" refers also to substances which are capable of exerting a biological effect in vitro and/or in vivo. The bioactive agents may be neutral or positively or negatively charged. Examples of suitable bioactive agents include diagnostic agents, pharmaceuticals, drugs, synthetic organic molecules, proteins, peptides, vitamins, steroids and genetic material, including nucleosides, nucleotides and polynucleotides.

"Diagnostic agent" refers to any agent which is used in connection with methods for diagnosing the presence or absence of a disease in a patient. Exemplary diagnostic agents include, for example, contrast agents for use in connection with ultrasound, magnetic resonance imaging or computed tomography of a patient.

"Genetic material" refers generally to nucleotides and polynucleotides, including deoxyribonucleic acid (DNA) and ribonucleic acid (RNA). The genetic material may be made by synthetic chemical methodology known to one of ordinary skill in the art, or by the use of recombinant technology, or by a combination of the two. The DNA and RNA may optionally comprise unnatural nucleotides and may be single or double stranded. "Genetic material" refers also to sense and anti-sense DNA and RNA, that is, a nucleotide sequence which is complementary to a specific sequence of nucleotides in DNA and/or RNA.

"Pharmaceutical" or "drug" refers to any therapeutic or prophylactic agent which is used in the treatment (including the prevention, diagnosis, alleviation, or cure) of a malady, affliction, disease or injury in a patient. Therapeutically useful peptides, polypeptides and polynucleotides are included within the meaning of the term pharmaceutical or drug.

"Stabilizing material" refers to a substance which is biocompatible and which is capable of promoting the formation of vesicles in a lipid composition. As used herein, "stabilizing material" refers also to a substance which is biocompatible and which is capable of improving the stability of a vesicle. In certain preferred embodiments, the stabilizing material comprises a polymer. "Polymer", as used herein, refers to molecules formed from the chemical union of two or more repeating units. Accordingly, included within the term "polymer" are, for example, dimers, trimers and oligomers. In certain other preferred embodiments, the stabilizing material comprises a non-polymeric material, including, for example, monomeric molecules. Encompassed also in the definition of "stabilizing material" are certain of the present bioactive agents. The stabilizing material may be neutral or positively or negatively charged. Preferred among the neutral stabilizing materials are polar materials.

"Vesicle stability" refers to the ability of gas-filled vesicles to retain the gas entrapped therein after being exposed, for about one minute, to a pressure of about 300 mm Hg. Vesicle stability is measured in percent (%), this being the fraction of the amount of gas which is originally entrapped in the vesicle and which is retained after release of the pressure. Vesicle stability includes reference also to "vesicle resilience" which refers to the ability of a vesicle to return to its original size after release of the pressure.

"Viscosity" refers to the internal friction of a fluid that is measurable using standard viscosity-measuring means, such as a viscometer.

"Raising viscosity" refers to the increase of viscosity by greater than about 20%.

"Non-covalent association" refers to intermolecular interaction among two or more separate molecules, which interaction does not involve a covalent bond. Intermolecular interaction is dependent upon a variety of factors, including, for example, the polarity of the involved molecules, the charge (positive or negative), if any, of the involved molecules, and the like. Non-covalent associations are preferably selected from the group consisting of ionic interaction, dipole—dipole interaction and van der Waal's forces and combinations thereof.

"Ionic interaction" refers to intermolecular interaction among two or more molecules, each of which is positively or negatively charged. Thus, for example, "ionic interaction" refers to the attraction between a first, positively charged molecule and a second, negatively charged molecule. Exemplary ionic interactions include, for example, the attraction between a negatively charged stabilizing material, for example, genetic material, and a positively charged lipid, for example, a cationic lipid, such as lauryltrimethylammonium bromide.

"Dipole-dipole interaction" refers generally to the attraction which can occur among two or more polar molecules. Thus, "dipole—dipole interaction" refers to the attraction of the positive end of a first polar molecule to the negative end of a second polar molecule. Dipole-dipole interactions are exemplified, for example, by the attraction between the electropositive head group, for example, the choline head group, of phosphatidylcholine and an electronegative atom, for example, a heteroatom, such as oxygen, nitrogen or sulphur, which is present in a stabilizing material, such as a polysaccharide. "Dipole-dipole interaction" refers also to intermolecular hydrogen bonding in which a hydrogen atom serves as a bridge between electronegative atoms on separate molecules and in which a hydrogen atom is held to a first molecule by a covalent bond and to a second molecule by electrostatic forces.

"Van der Waal's forces" refers to the attractive forces between non-polar molecules that are accounted for by quantum mechanics. Van der Waal's forces are generally associated with momentary dipole moments which are induced by neighboring molecules and which involve changes in electron distribution.

"In combination with" refers to the incorporation of a bioactive agent with a lipid composition of the present invention. The bioactive agent can be combined with the lipid composition in any of a variety of ways. For example, when the lipid composition is in the form of a vesicular composition, the bioactive agent may be entrapped within the internal void of the vesicle. The bioactive agent may also be integrated within the layer(s) or wall(s) of the vesicle, for example, by being interspersed among lipids which are contained within the vesicular layer(s) or wall(s). In addition, it is contemplated that the bioactive agent may be located on the surface of a vesicle. In this case, the bioactive agent may interact chemically with the surface of the vesicle and remain substantially adhered thereto. Such interaction may take the form of, for example, non-covalent association. In certain embodiments, the interaction may result in the stabilization of the vesicle.

"Coat" or "coating" refers to the interaction of the stabilizing material with the lipid and/or vesicles and includes non-covalent interaction.

The present invention is directed, in part, to stabilized lipid compositions. The lipid compositions comprise, in an aqueous carrier, a lipid and a material which is capable of stabilizing the composition. The stabilizing material is associated non-covalently with the lipid and is present in the composition in an amount sufficient to coat the lipid but insufficient to raise the viscosity of the composition.

It has been surprisingly and unexpectedly found that when combined with lipid compounds, the present stabilizing materials are capable of promoting the formation of vesicles. In addition, the stabilizing materials are surprisingly and unexpectedly capable of improving the stability of the formed vesicles. In contrast to prior art techniques for stabilizing lipid compositions, the present methods and compositions provide stabilizing materials which associate non-covalently with lipids. Accordingly, the present invention provides simple and efficient methods for stabilizing lipid compositions, especially vesicular compositions.

A variety of lipid compounds can be employed in the present compositions. Preferred lipid compounds are those which, when combined with the present stabilizing materials, tend to form vesicles. Suitable lipids include, for example, phospholipids, such as phosphatidylcholine with both saturated and unsaturated fatty acids including dioleoylphosphatidylcholine; dimyristoylphosphatidylcholine; dipalmitoylphosphatidylcholine; distearoylphosphatidylcholine; phosphatidylethanolamines, such as dipalmitoylphosphatidylethanolamine, dioleoylphosphatidylethanolamine, N-succinyldioleoylphosphatidylethanolamine and 1-hexadecyl-2-palmitoylglycerophosphoethanolamine; phosphatidylserine; phosphatidylglycerol; sphingolipids; glycolipids, such as ganglioside GM1; glucolipids; sulfatides; glycosphingolipids; phosphatidic acids, such as dipalmitolylphosphatidic acid; palmitic acid; stearic acid; arachidonic acid; oleic acid; lipids bearing polymers such as polyethyleneglycol or polyvinylpyrrolidone; cholesterol and cholesterol hemisuccinate; 12-(((7'-diethylaminocoumarin-3-yl)carbonyl)methylamino)octadecanoic acid; N-[12-(((7'-diethylaminocoumarin-3-yl)carbonyl)methylamino) octadecanoyl]-2-aminopalmitic acid; cholesteryl)4'-trimethylamino)butanoate; 1,2-dioleoyl-sn-glycerol; 1,2- dipalmitoyl-sn-3-succinylglycerol; 1,3-dipalmitoyl-2-succinylglycerol; and palmitoylhomocysteine.

Suitable lipid compounds include also lipids used to make mixed micelle systems, such as laurytrimethylammonium bromide; cetyltrimethylammonium bromide; myristyltrimetheylammonium bromide; alkyldimethylbenzylammonium chloride (where alkyl is, for example, $C_{12}$, $C_{14}$ or $C_{15}$); benzyldimethyldodecylammonium bromide/chloride; benzyldimethylhexadecylammonium bromide/chloride; benzyldimethyltetradecylammonium bromide/chloride; cetyldimethylethylammonium bromide/chloride; and cetylpyridinium bromide/chloride.

Suitable lipids for use in the present compositions include also lipids carrying a net charge, for example, anionic and/or cationic lipids. Exemplary cationic lipids include, for example, N-[1-(2,3-dioleoyloxy)propyl]-N,N,N-trimethylammonium chloride) (DOTMA), dioleoyloxy-3-(trimethylammonium)propane) (DOTPA) and 1,2,-dioleoyloxy-e-(4'-trimethylammonium)butanoyl-sn-glycerol.

In addition to, or instead of, the lipid compounds described above, the present lipid compositions may comprise aliphatic carboxylic acids, for example, fatty acids. Preferred fatty acids include those which contain about 5 to about 22 carbon atoms in the aliphatic group. The aliphatic group can be either linear or branched. Exemplary saturated fatty acids include, for example, (iso)lauric, (iso)myristic, (iso)palmitic and (iso)stearic acids. Exemplary unsaturated fatty acids include, for example, lauroleic, physeteric, myristoleic, palmitoleic, petroselinic, and oleic acid. Suitable fatty acids include also, for example, fatty acids in which the aliphatic group is an isoprenoid or prenyl group. In addition, carbohydrates bearing polymers may be used in the present lipid compositions. Carbohydrate beating lipids are described, for example, in U.S. Pat. No. 4,310,505, the disclosures of which are hereby incorporated by reference herein, in their entirety.

Other lipid compounds for use in the present lipid compositions, in addition to those exemplified above, would be apparent in view of the present disclosure. Preferably, the lipids from which the lipid compositions are prepared are selected to optimize certain desirable properties of the compositions, including serum stability and plasma half-life. The selection of suitable lipids in the preparation of lipid compositions, in addition to the lipids exemplified above, would be apparent to one skilled in the art and can be achieved without undue experimentation, based on the present disclosure.

The concentration of lipid in the present lipid compositions can vary and depends upon various factors, including, for example, the particular lipid(s) and stabilizing material (s) which are employed in the compositions. It has been unexpectedly and surprisingly found that, due to the incorporation of stabilizing materials as described herein, vesicles are formed with substantially low concentrations of lipid. This is beneficial in that the amount of lipid compound which is administered to a patient is reduced. In addition, the cost associated with the manufacture of the present lipid compositions is desirably reduced by virtue of the lower amounts of raw ingredient, such as lipid, which are required. Thus, in the case of vesicular compositions, such as liposomes and micelles, it has been found that stable vesicles are provided which comprise only a single bilayer or monolayer. In general, the concentration of lipid in the present lipid compositions is from about 0.001 mg/mL to about 200 mg/mL, with a concentration of about 0.01 mg/mL to 20 mg/mL being preferred. More preferably, the concentration of lipid compound is about 0.05 mg/mL to about 10 mg/mL, with a concentration of about 0.1 mg/mL to about 5 mg/mL being even more preferred.

In accordance with the present invention, the lipid compositions further comprise a stabilizing material. It has been unexpectedly found that stabilizing materials, as defined herein, are capable of promoting the formation of vesicles in a lipid composition. Thus, when the stabilizing materials are combined with lipid compounds according to the methods described herein, the lipid compounds will desirably aggregate to form vesicles. As noted above, vesicle concentration is important with respect to the effectiveness of contrast agents based on vesicles. When combined with lipid compounds, the present stabilizing materials desirably promote the formation of vesicles in a concentration that affords effective contrast agents. Preferably, the present stabilizing materials provide lipid compositions having a vesicle concentration of greater than about $1 \times 10^8$ vesicles/mL. More preferably, the present stabilizing materials provide vesicle concentrations of greater than about $1'10^9$ vesicles/mL.

The stabilizing materials improve also the stability of the formed vesicles. Preferably, the present stabilizing materials provide vesicles having a stability of greater than about 50%. More preferably, the present stabilizing materials provide vesicles have a stability of at least about 75%, with a stability of at least 90% being more preferred.

In certain embodiments, the stabilizing material comprises a polymer. Preferred polymers include polymers in which the repeating units contain one or more hydroxy groups (polyhydroxy polymers); polymers in which the repeating units contain one or more amino groups (polyamine polymers); polymers in which the repeating units contain one or more carboxy groups (polycarboxy polymers); and polymers in which the repeating units contain one or more saccharide moieties (polysaccharide polymers). The molecular weight of the polymers may vary, and is generally about 50 to about 5,000,000, with polymers having a molecular weight of about 100 to about 50,000 being preferred. More preferred polymers have a molecular weight of about 150 to about 10,000, with molecular weights of 800 to about 8,000 being even more preferred.

The stabilizing materials comprise neutral or positively or negatively charged materials. Preferred among the neutral stabilizing materials include lipidic and/or oily materials, polyalcohol polymers, glycosaminoglycans, carbohydrates, including monosaccharides, disaccharides and polysaccharides, gums and cellulosic materials. Exemplary neutral stabilizing materials include, for example, oils, such as peanut oil, canola oil, olive oil, safflower oil and corn oil; lecithin; sphingomyelin; cholesterol and derivatives thereof; squalene; terpenes and terpenoid compounds; triglycerides; gums, such as xanthan, tragacanth, locust bean, guar and carrageenan gums; methoxylated pectin; starch; agarose; cellulose and semi-synthetic cellulose, for example, methyl cellulose, hydroxyethyl cellulose, methoxy cellulose and hydroxypropyl cellulose; acacia; agar; bentonites, including purified bentonite; magma; carbomer 934P; dextrin; gelatin; di- and trihydroxy substituted alkanes and their polymers, including polyvinylalcohol; mono-, di- and triglycerides; amino alcohols; monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose.

Suitable positively charged stabilizing materials include compounds containing, for example, protonated or quaternary amino groups, including polymers in which the repeating units contain one or more amino groups, such as peptides, polypeptides, proteins and lipoproteins, such as albumin and natural lipoproteins. Exemplary positively charged stabilizing materials include, for example, chitin; alkanolamines, such as monoethanolamine, diethanolamine and triethanolamine, and mixtures thereof, including, for example, trolamine; polylysine; polyarginine; polyethyleneimine; chitosan; and peptides, including melanin concentrating hormone and dynorphin. Suitable negatively charged materials are compounds containing, for example, carboxy ($CO_2^-$ groups, including polycarboxy polymers. Exemplary negatively charged stabilizing materials include, for example, carboxymethylcellulose; salts of alginic acid, such as sodium and calcium alginate; salts of glycosaminoglycans, including salts of hyaluronic acid; phosphorylated and sulfonated derivatives of carbohydrates; genetic material, such as interleukin-2 and interferon; phosphorothioate oligomers; and negatively charged peptides, such as deltorphin.

Other stabilizing materials, in addition to those exemplified above, would be apparent to one of ordinary skill in the art based on the present disclosure.

An important aspect of the present invention is that the stabilizing materials are associated non-covalently with the lipids. Accordingly, stabilization of the lipid compositions can be achieved by combining together the lipids and stabilizing materials according to the methods described herein and which generally involve admixing together the lipids and stabilizing materials. Stabilization is achieved by the coating of the lipid with the stabilizing material. Thus, the methods and compositions of the present invention avoid the necessity of covalently linking together lipids and stabilizing materials through involved and complex chemical reactions, such covalent linking reactions being the subject of, for example, prior art attempts to stabilize compositions. See, e.g., Klaveness et al., WO 92/17212. The stabilizing materials preferably associate with the lipids via one or more of the following modes of interaction: ionic interaction, dipole—dipole interaction and van der Waals forces and combinations thereof.

While the inventor does not wish to be bound by any theory or theories, it is believed that the stabilizing materials promote formation of vesicles and stabilize the formed vesicles in the following manner. The stabilizing materials employed herein, whether neutral or positively or negatively charged, generally comprise hydrophobic and hydrophilic domains. It is believed that, in the present lipid compositions, the stabilizing materials associate with the lipids such that the hydrophobic domains of the stabilizing materials interact with the hydrophobic domains of the lipid and the hydrophilic domains of the stabilizing materials interact with the hydrophilic domains of the lipids. Similar interactions are believed to occur between, for example, positively charged regions of polyamine stabilizing materials and negatively charged regions, such as carboxy groups, of fatty acids. This interaction contributes to the formation of vesicles. Once the vesicles are formed, it is believed that the stabilizing materials coat the vesicle such that the hydrophobic domains of the stabilizing materials interact with the generally hydrophobic surface or other hydrophobic areas of the vesicle and the hydrophilic domains of the stabilizing materials are directed outwardly into the aqueous milieu. The vesicles are thus protected in, for example, a "stabilizing cocoon", which operates by shielding the vesicles from substances that would otherwise cause their rupture.

As noted above, the stabilizing materials are highly effective in promoting the formation of vesicles from substantially low concentrations of lipid compound. Thus, another beneficial aspect of the present methods and compositions is that stable, thin-walled vesicles are provided which possess desirable elasticity and deformability. Thus, the present compositions provide vesicles which can readily deform to squeeze through blood vessels; the risk of occlusion of vessels is thereby reduced.

The concentration of the stabilizing material in the present lipid compositions can vary and depends upon the particular lipids and/or stabilizing materials which are employed. It is preferred that the concentration of stabilizing material is at least sufficient to achieve coating of the lipid but insufficient to raise the viscosity of the lipid composition. In preferred embodiments, the concentration of stabilizing material is from about 0.01 mg/mL to about 200 mg/mL. More preferably, the concentration of stabilizing material is from about 0.05 mg/mL to about 5 mg/mL with concentrations of about 15 mg/mL to about 2.5 mg/mL being even more preferred.

It has been surprisingly and unexpectedly found that the stabilizing effect provided by the present stabilizing materials is substantially independent of viscosity. In this connection, it has been found that viscosity is not raised (that is, not raised by greater than about 20%) after the present stabilizing materials have been added to a composition that contains lipid alone (no stabilizing material) to form the compositions of the present invention. This is surprising since prior art stabilizing materials generally produce a significant change in the viscosity of lipid compositions, with a general tendency towards increased viscosities. Preferably, the viscosity is not raised by greater than about 15%, with a raise in viscosity of no greater than about 10% being more preferred. Even more preferably, the viscosity is not raised by greater than about 5%, with no raise in viscosity (0%) being still more preferred.

In certain embodiments of the invention, it has been found that the viscosity is decreased after the present stabilizing materials have been added to a composition that contains lipid alone (no stabilizing material) to form the compositions of the present invention. This is particularly surprising and unexpected since, as noted above, the addition of prior art stabilizing materials to compositions that contain lipid alone (no stabilizing material) generally results in increased viscosities. Preferably, the viscosity is decreased by about 5% or more, with a decrease in viscosity of about 10% or more being more preferred. Even more preferably, the viscosity is decreased by about 15% or more, with a decrease in viscosity of about 20% or more being still more preferred.

In certain preferred embodiments of the invention, the lipid compositions comprise a vesicular composition. The vesicular compositions may comprise micelles and/or liposomes. A wide variety of methods are available for the preparation of vesicular compositions, including, for example, shaking, drying, gas-installation, spray drying, and the like. Suitable methods for preparing the vesicular compositions are described, for example, in U.S. application Ser. No. 307,305, filed Sep. 16, 1994, the disclosures of which are incorporated herein by reference. Preferably, the vesicles are prepared from lipids which remain in the gel state. The following table lists some of the representative lipids and their phase transition temperatures.

TABLE I

Saturated Diacyl-sn-Glycero-3-Phosphocholines:
Main Chain Melting Transition Temperatures

| # Carbons in Acyl Chains | Main Phase Transition Temperature (°C.) |
|---|---|
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

See, for example, Derek Marsh, CRC *Handbook of Lipid Bilayers*, p. 139 (CRC Press, Boca Raton, Fla. 1990).

With particular reference to the preparation of micelle compositions, the following discussion is provided. Micelles may be prepared using any one of a variety of conventional micellar preparatory methods which will be apparent to those skilled in the art. These methods typically involve suspension of the lipid compound in an organic solvent, evaporation of the solvent, resuspension in an aqueous medium, sonication and centrifugation. The foregoing methods, as well as others, are discussed, for example, in Canfield et al., *Methods in Enzymology*, Vol. 189, pp. 418–422 (1990); El-Gorab et al, *Biochem. Biophys. Acta*, Vol. 306, pp. 58–66 (1973); *Colloidal Surfactant*, Shinoda, K., Nakagana, Tamamushi and Isejura, Academic Press, N.Y. (1963) (especially "The Formation of Micelles", Shinoda, Chapter 1, pp. 1–88); *Catalysis in Micellar and Macromolecular Systems*, Fendler and Fendler, Academic Press, N.Y. (1975). The disclosures of each of the foregoing publications are incorporated by reference herein, in their entirety.

As noted above, the vesicular composition may comprise liposomes. In any given liposome, the lipid compound(s) may be in the form of a monolayer or bilayer, and the mono- or bilayer lipids may be used to form one or more mono- or bilayers. In the case of more than one mono- or bilayer, the mono- or bilayers are generally concentric. Thus, the lipids may be used to form a unilamellar liposome (comprised of one monolayer or bilayer), an oligolamellar liposome (comprised of two or three monolayers or bilayers) or a multilamellar liposome (comprised of more than three monolayers or bilayers).

A wide variety of methods are available in connection with the preparation of liposome compositions. Accordingly, the liposomes may be prepared using any one of a variety of conventional liposome preparatory techniques which will be apparent to those skilled in the art. These techniques include solvent dialysis, French press, extrusion (with or without freeze-thaw), reverse phase evaporation, microemulsification and simple freeze-thawing. The liposomes may also be prepared by various processes which involve shaking or vortexing. This may be achieved, for example, by the use of a mechanical shaking device, such as a Wig-L-Bug™ (Crescent Dental, Lyons, Ill.). Conventional microemulsification equipment, such as a Microfluidizer™ (Microfluidics, Woburn, Mass.) may be used also.

Additional methods for the preparation of liposome compositions include, for example, sonication, chelate dialysis, homogenization, solvent infusion, spontaneous formation, solvent vaporization, controlled detergent dialysis, and others, each involving the preparation of liposomes in various fashions. Methods which involve freeze-thaw techniques are preferred in connection with the preparation of liposomes. Suitable freeze-thaw techniques are described, for example, in copending U.S. application Ser. No. 07/838,504, filed Feb. 19, 1992, the disclosures of which are incorporated herein by reference in their entirety. Preparation of the liposomes may be carded out in a solution, such as an aqueous saline solution, aqueous phosphate buffer solution, or sterile water.

The size of the liposomes can be adjusted, if desired, by a variety of techniques, including extrusion, filtration, sonication and homogenization. In addition, the size of the liposomes can be adjusted by the introduction of a laminar stream of a core of liquid into an immiscible sheath of liquid. Other methods for adjusting the size of the liposomes and for modulating the resultant liposomal biodistribution and clearance of the liposomes would be apparent to one skilled in the art based on the present disclosure. Preferably, the size of the liposomes is adjusted by extrusion under pressure through pores of a defined size. Although liposomes employed in the subject invention may be of any one of a variety of sizes, preferably the liposomes are small, that is, less than about 100 nanometer (nm) in outside diameter.

Many of the foregoing liposomal preparatory techniques, as well as others, are discussed, for example, in U.S. Pat. No. 4,728,578; U.K. Patent Application GB 2193095 A; U.S. Pat. No. 4,728,575; U.S. Pat. No. 4,737,323; International Application Serial No. PCT/US85/01161; Mayer et al., *Biochimica et Biophysica Acta*, Vol. 858, pp. 161–168 (1986); Hope et al., *Biochimica et Biophysica Acta*, Vol. 812, pp. 55–65 (1985); U.S. Pat. No. 4,533,254; Mayhew et al., *Methods in Enzymology*, Vol. 149, pp. 64–77 (1987); Mayhew et al., *Biochimica et Biophysica Acta*, Vol 755, pp. 169–74 (1984); Cheng et al, *Investigative Radiology*, Vol. 22, pp. 47–55 (1987); International Application Serial No. PCT/US89/05040; U.S. Pat. No. 4,162,282; U.S. Pat. No. 4,310,505; U.S. Pat. No. 4,921,706; and *Liposome Technology*, Gregoriadis, G., ed., Vol. I, pp. 29–31, 51–67 and 79–108 (CRC Press Inc., Boca Raton, Fla. 1984), the disclosures of each of which are hereby incorporated by reference herein, in their entirety.

Although any of a number of varying techniques can be used, the vesicular compositions of the present invention are preferably prepared using a shaking technique. Preferably, the shaking technique involves agitation with a mechanical shaking apparatus, such as a Wig-L-Bug™ (Crescent Dental, Lyons, Ill.), such as those disclosed in copending U.S. application Ser. No. 160,232, filed Nov. 30, 1993 (U.S. Pat. No. 5,542,935), the disclosures of which are hereby incorporated herein by reference in their entirety.

As those skilled in the art will recognize, any of the lipid compositions and/or lipid formulations may be lyophilized for storage, and reconstituted in, for example, with an aqueous medium (such as sterile water or phosphate buffered solution, or aqueous saline solution), with the aid of vigorous agitation. To prevent agglutination or fusion of the lipids as a result of lyophilization, it may be useful to include additives which prevent such fusion or agglutination from occurring. Additives which may be useful include sorbitol, mannitol, sodium chloride, glucose, trehalose, polyvinylpyrrolidone and poly(ethylene glycol), for example, PEG 400. These and other additives are described in the literature, such as in the U.S. Pharmacopeia, USP XXII, NF XVII. The United States Pharmacopeia, The National Formulary, United States Pharmacopeial Convention Inc., 12601 Twinbrook Parkway, Rockville, Md. 20852, the disclosures of which are hereby incorporated herein by reference in their entirety. Lyophilized preparations generally have the advantage of greater shelf life.

In preferred embodiments of the present invention, a gas, such as an inert gas, is incorporated in the lipid compositions. The gases provide the lipid compositions with enhanced reflectivity, particularly in vesicular composition in which the gas is entrapped within the vesicles. This increases their effectiveness as contrast agents.

Preferred gases are gases which are inert and which are biocompatible, that is, gases which are not injurious to biological function. Preferable gases include those selected from the group consisting of air, noble gases, such as helium, neon, argon and xenon, carbon dioxide, nitrogen, fluorine, oxygen, sulfur hexafluoride, fluorocarbons, perfluorocarbons, and mixtures thereof. Other gases, including the gases exemplified above, would be readily apparent to one skilled in the art based on the present disclosure. In preferred embodiments, the gas comprises a perfluorocarbon. Preferably, the perfluorocarbon is selected from the group consisting of perfluoromethane, perfluoroethane, perfluoropropane, perfluorobutane, perfluorocyclobutane and mixtures thereof. More preferably, the perfluorocarbon gas is perfluoropropane or perfluorobutane, with perfluoropropane being particularly preferred. Another preferable gas is sulfurtetrafluoride.

In certain preferred embodiments, a gas, for example, air or a perfluorocarbon gas, is combined with a liquid perfluorocarbon, such as perfluorohexane, perfluoroheptane, perfluorooctylbromide (PFOB), perfluorodecalin, perfluorododecalin, perfluorooctyliodide, perfluorotripropylamine and perfluorotributylamine.

It may also be desirable to incorporate in the lipid compositions a precursor to a gaseous substance. Such precursors include materials that are capable of being converted in vivo to a gas. Preferably, the gaseous precursor is biocompatible, and the gas produced in vivo is biocompatible also.

Among the gaseous precursors which are suitable for use in the present compositions are pH sensitive agents. These agents include materials that are capable of evolving gas, for example, upon being exposed to a pH that is neutral or acidic. Examples of such pH sensitive agents include salts of an acid which is selected from the group consisting of inorganic acids, organic acids and mixtures thereof. Carbonic acid ($H_2CO_3$) is an example of a suitable inorganic acid, and aminomalonic acid is an example of a suitable organic acid. Other acids, including inorganic and organic acids, would be readily apparent to one skilled in the art based on the present disclosure.

Preferably, the gaseous precursor is a salt which is selected from the group consisting of an alkali metal salt, an ammonium salt and mixtures thereof. More preferably, the salt is selected from the group consisting of carbonate, bicarbonate, sesquecarbonate, aminomalonate and mixtures thereof.

Examples of gaseous precursor materials for use in the lipid compositions of the present invention include lithium carbonate, sodium carbonate, potassium carbonate, lithium bicarbonate, sodium bicarbonate, potassium bicarbonate, magnesium carbonate, calcium carbonate, magnesium bicarbonate, ammonium carbonate, ammonium bicarbonate, ammonium sesquecarbonate, sodium sesquecarbonate, sodium aminomalonate and ammonium aminomalonate. Aminomalonate is well known in the art, and its preparation is described, for example, in Thanassi, *Biochemistry*, Vol. 9, no. 3, pp. 525–532 (1970); Fitzpatrick et al., *Inorganic Chemistry*, Vol. 13, no. 3 pp. 568–574 (1974); and Stelmashok et al., *Koordinatsionnaya Khimiya*, Vol. 3, no. 4, pp. 524–527 (1977). The disclosures of these publications are hereby incorporated herein by reference.

In addition to, or instead of, being sensitive to changes in pH, the gaseous precursor materials may also comprise compounds which are sensitive to changes in temperature. Such temperature sensitive agents include materials which have a boiling point of greater than about 37° C. Exemplary temperature sensitive agents are methyl lactate, perfluoropentane and perfluorohexane. The gaseous precursor materials may be also photoactivated materials, such as diazonium ion and aminomalonate. As discussed more fully hereinafter, certain lipid compositions, and particularly vesicular compositions, may be designed so that gas is formed at the target tissue or by the action of sound on the particle. Examples of gaseous precursors are described, for example, in U.S. Pat. Nos. 5,088,499 and 5,149,319. The disclosures of these patents are hereby incorporated herein by reference in their entirety. Other gaseous precursors, in addition to those exemplified above, will be apparent to one skilled in the art based on the present disclosure.

The gaseous substances and/or gaseous precursors are preferably incorporated in the lipid compositions of the present invention irrespective of the physical nature of the composition. Thus, it is contemplated that the gaseous substances and/or precursors thereto are incorporated in compositions in which the lipids are aggregated, for example, substantially randomly, as well as compositions in which the lipids form vesicles, including micelles and liposomes. Incorporation of the gaseous substances and/or precursors thereto in the lipid compositions may be achieved by using any of a number of methods. For example, the formation of gas-filled vesicles can be achieved by shaking or otherwise agitating an aqueous mixture which comprises a gas or gas precursor and the lipids of the present invention. This promotes the formation of stabilized vesicles within which the gas or gas precursor is encapsulated.

In addition, a gas may be bubbled directly into an aqueous mixture of the present lipid compounds. Alternatively, a gas instillation method can be used as disclosed, for example, in U.S. Pat. Nos. 5,352,435 and 5,228,446, the disclosures of each of which are hereby incorporated herein by reference in their entirety. Suitable methods for incorporating the gas or gas precursor in cationic lipid compositions are disclosed also in U.S. Pat. No. 4,865,836, the disclosure of which is hereby incorporated herein by reference. Other methods would be apparent to one skilled in the art based on the present disclosure. Preferably, the gas is instilled in the lipid compositions after or during the addition of the stabilizing material and/or during formation of vesicles.

In preferred embodiments, the gaseous substances and/or gaseous precursor materials are incorporated in vesicular compositions, with micelles and liposomes being preferred. As discussed in detail below, vesicles in which a gas or gas precursor or both are encapsulated are advantageous in that they provide improved reflectivity in vivo.

In certain embodiments of the present invention, the compositions further comprise a bioactive agent. These compositions are referred to herein as "lipid formulations", and can be used for the therapeutic delivery in vivo of bioactive agents. Preferably, the lipid formulations comprise vesicular formulations. In vesicular formulations, circulation and delivery of the vesicles to the targeted tissue can be observed via a non-invasive procedure. In connection with gas precursor- or gas-filled vesicles, the application of high energy ultrasound, radio frequency, optical energy, for example, laser light, and/or heat, to produce areas of hyperthermia, can be used, if desired, to rupture in vivo the vesicles and thereby promote release of the entrapped gas (or precursor thereto) and bioactive agent. Thus, vesicular formulations permit the controlled release of a bioactive agent in vivo.

It has been found that certain bioactive agents, which are desirably administered to a patient in connection with the diagnosis, treatment and/or prophylaxis of a disease, also desirably stabilize the lipid compositions. In these embodiments, the bioactive agent is acting as both a stabilizing material and as a diagnostic or therapeutic material. These bioactive agents are generally capable of associating non-covalently with the lipid compounds, such non-covalent interaction including, for example, ionic interaction, dipole—dipole interaction and van der Waal's force and combinations thereof. Particularly suitable bioactive agents for use in the present lipid formulations, and which also act as stabilizing materials, include, for example, genetic material, such as DNA and RNA, peptides and pharmaceuticals or drugs, such as nalidixic acid and vincristine.

In the case of vesicular compositions, including micelles and liposomes, it is contemplated that the bioactive agent is entrapped within the vesicle of the liposome or micelles. In certain cases, the bioactive agent can be incorporated also into the membrane walls of the vesicle. In the case of lipid compositions in which the lipids are substantially aggregated randomly, or substantially not aggregated, it is contemplated that the bioactive agent is generally dispersed homogeneously throughout the composition.

In certain embodiments, it is desirable to incorporate in the lipid compositions materials which comprise a stabilizing material, for example, a polymer, such as an alginic acid polymer, that is covalently linked to a bioactive agent. An example of such a stabilizing material is nalidixic acid alginate in which a stabilizing material (alginic acid polymer) is covalently linked to a bioactive material (nalidixic acid). Such stabilizing materials are desirable in that they are capable of stabilizing the lipid compositions, as well as providing a source of bioactive agent. In this connection, it is contemplated that stabilization of lipid compositions is achieved by such stabilizing materials, as discussed above. It is contemplated also that after administration, the stabilizing materials are hydrolyzed in vivo, to bioactive agent (nalidixic acid) and stabilizing material (alginic acid).

In certain circumstances, it is desirable to incorporate one or more charged species into the lipid compositions. As discussed below, such charged species contribute to the stabilizing effect provided by certain of the present stabilizing materials. Examples of suitable charged species include, for example, cations, such as metal ions, or anions. Exemplary cations include, for example, calcium, manganese, magnesium, copper, gadolinium or dysprosium cations, or any other cation which is compatible for use in connection with pharmaceutical applications. Suitable anions include, for example, sulphur, peroxides or superoxides. The anionic species may be chelated with chelating agents, for example, ethylenediaminetetraacetic acid (EDTA) and diethylenetriaminepentaacetic acid (DTPA).

While the inventor does not wish to bound by any theory or theories, it is believed that the charged species described above are capable of forming bridges, for example, ionic bridges, between the lipids and the stabilizing materials. Thus, for example, an anion, such as sulphur, can associate non-covalently with a positively charged lipid, for example, DOTMA, and a positively charged stabilizing material, for example, polylysine.

In addition to the stabilizing materials which are discussed above and which are associated non-covalently with the lipids, it is desirable, in certain embodiments, to include stabilizing materials which are covalently associated with the lipids. Such covalently bound stabilizing materials may take the form of, for example, stabilizing materials bearing polymers, including lipids, proteins and/or saccharides bearing polymers. Exemplary polymers include hydrophilic polymers, such as poly(ethyleneglycol) (PEG), poly(vinylpyrrolidine), polyoxomers and polysorbate and poly(vinylalcohol). Preferred among the PEG polymers are PEG 2000, PEG 5000 and PEG 8000, which have molecular weights of 2000, 5000 and 8,000 respectively. Other suitable polymers, hydrophilic and otherwise, will be readily apparent to those skilled in the art based on the present disclosure. Polymers which may be incorporated via alkylation or acylation reactions with a lipid are particularly useful for improving the stability of the lipid compositions. Exemplary lipids which bear hydrophilic polymers include, for example, dipalmitoylphosphatidylethanolamine-PEG, dioleoylphosphatidylethanolamine-PEG and distearylphosphatidylethanolamine-PEG.

Other materials for use in the preparation of stabilized lipid compositions, in addition to those exemplified above, would be apparent to one skilled in the art based on the present disclosure. For example, it may be desirable to include in the lipid compositions anti-bactericidal agents and/or preservatives. Examples of these materials include, for example, sodium benzoate, quaternary ammonium salts, sodium azide, methyl paraben, propyl paraben, sorbic acid, ascorbyl, palmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulphur dioxide and organic mercurial salts.

It may be desirable to also include materials which contribute to the stability of the lipid compositions and/or the formation of vesicular compositions. Exemplary of such materials are nonionic materials, including, for example, polyoxyethylene fatty acid esters, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers and polyoxyethylene fatty acid stearates.

As noted above, there exists a wide variety of techniques for the preparation of lipid compositions according to the present invention. Similarly, a wide variety of techniques exist for the preparation of lipid formulations. For example, the lipid formulations may be prepared from a mixture of lipid compounds, bioactive agent and gas or gaseous precursor. In this case, lipid compositions are prepared as described above in which the compositions comprise also bioactive agent. Thus, for example, micelles can be prepared in the presence of a bioactive agent. In connection with lipid compositions which comprise a gas, the preparation can involve, for example, bubbling a gas directly into a mixture of the lipid compounds and stabilizing material. Alternatively, the lipid compositions may be preformed from lipid compounds and gas or gaseous precursor. In the latter case, the bioactive agent is then added to the lipid composition prior to use. For example, an aqueous mixture of liposomes and gas may be prepared to which the bioactive agent is added and which is agitated to provide the liposome formulation. The liposome formulation is readily isolated also in that the gas- and/or bioactive agent-filled liposome vesicles generally float to the top of the aqueous solution. Excess bioactive agent can be recovered from the remaining aqueous solution.

The formulations of the present invention can be used in either in vitro or in vivo applications. In the case of in vitro applications, including cell culture applications, the lipid formulations can be added to the cells in cultures and then incubated. If desired, where liposomes are employed, energy, such as sonic energy, may be applied to the culture media to burst the liposomes and release any therapeutic agents.

With respect to in vivo applications, the formulations of the present invention can be administered to a patient in a variety of forms adapted to the chosen route of administration, namely, parenterally, orally, or intraperitoneally. Parenteral administration, which is preferred, includes administration by the following routes: intravenous; intramuscular; interstitially; intra-arterially; subcutaneous; intraocular; intrasynovial; transepithelial, including transdermal; pulmonary via inhalation; ophthalmic; sublingual and buccal; topically, including ophthalmic; dermal; ocular; rectal; and nasal inhalation via insufflation. Intravenous administration is preferred among the routes of parenteral administration.

In the case of diagnostic applications such as ultrasound, the lipid compositions, which may further comprise a gas or gaseous precursor, are administered to a patient. Energy, preferably in the form of ultrasonic energy, is applied to at least a portion of the patient to image the target tissue. A visible image of an internal region of the patient is then obtained, such that the presence or absence of diseased tissue can be ascertained.

Ultrasonic imaging techniques, including second harmonic imaging, are well known in the art, and are described, for example, in Uhlendorf, "Physics of Ultrasound Contrast Imaging: Scattering in the Linear Range", *IEEE Transactions on Ultrasonics, Ferroelectrics, and Frequency Control*, Vol. 14(1), pp. 70–79 (1994) and Sutherland, et al., "Color Doppler Myocardial Imaging: A New Technique for the Assessment of Myocardial Function", *Journal of the American Society of Echocardiography*, Vol. 7(5), pp. 441–458 (1994), the disclosures of which are hereby incorporated herein by reference in their entirety.

Ultrasound can be used for both diagnostic and therapeutic purposes. In general, the levels of energy from diagnostic ultrasound are insufficient to cause rupture of vesicular species and to facilitate release and cellular uptake of the bioactive agents. Moreover, diagnostic ultrasound involves the application of one or more pulses of sound. Pauses between pulses permits the reflected sonic signals to be received and analyzed. The limited number of pulses used in diagnostic ultrasound limits the effective energy which is delivered to the tissue that is being studied.

On the other hand, higher energy ultrasound, for example, ultrasound which is generated by therapeutic ultrasound equipment, is generally capable of causing rupture of the vesicular species. In general, therapeutic ultrasound machines use from about 10 to about 100% duty cycles, depending on the area of tissue to be treated with the ultrasound. Areas of the body which are generally characterized by larger amounts of muscle mass, for example, backs and thighs, as well as highly vascularized tissues, such as heart tissue, may require a larger duty cycle, for example, up to about 100%.

In therapeutic ultrasound, continuous wave ultrasound is used to deliver higher energy levels. For the rupture of vesicular species, continuous wave ultrasound is preferred, although the sound energy may be pulsed also. If pulsed sound energy is used, the sound will generally be pulsed in echo Wain lengths of about 8 to about 20 or more pulses at a time. Preferably, the echo train lengths are about 20 pulses at a time. In addition, the frequency of the sound used may vary from about 0.25 to about 100 megahertz (MHz). In general, frequency for therapeutic ultrasound ranges between about 0.75 and about 3 MHz are preferred with about 1 and about 2 MHz being more preferred. In addition, energy levels may vary from about 0.5 Watt (W) per square centimeter ($cm^2$) to about 5.0 W/cm:, with energy levels of about 0.5 to about 2.5 W/cm: being preferred. Energy levels for therapeutic ultrasound involving hyperthemia are generally from about 5 W/$cm^2$ to about 50 W/$cm^2$. For very small vesicular species, for example, species in which the vesicles have a diameter of less than about 0.5 micron, higher frequencies of sound are generally preferred. This is because smaller vesicular species are capable of absorbing sonic energy more effectively at higher frequencies of sound. When very high frequencies are used, for example, greater than about 10 MHz, the sonic energy will generally penetrate fluids and tissues to a limited depth only. Thus, external application of the sonic energy may be suitable for skin and other superficial tissues. However, for deep structures it is generally necessary to focus the ultrasonic energy so that it is preferentially directed within a focal zone. Alternatively, the ultrasonic energy may be applied via interstitial probes, intravascular ultrasound catheters or endoluminal catheters. Such probes or catheters may be used, for example, in the esophagus for the diagnosis and/or treatment of esophageal carcinoma. In addition to the therapeutic uses discussed above, the present compositions can be employed in connection with esophageal carcinoma or in the coronary arteries for the treatment of atherosclerosis, as well as the therapeutic uses described, for example, in U.S. Pat. No. 5,149,319, the disclosures of which are hereby incorporated herein by reference in their entirety.

The useful dosage to be administered and the particular mode of administration will vary depending upon such factors as the age, weight and the particular animal and region thereof to be treated, the particular lipid compound and stabilizing material used, the presence or absence of a bioactive agent, the diagnostic or therapeutic use contemplated, and the form of the formulation, for example, micelle or liposome, as will be readily apparent to those skilled in the art. Typically, dosage is administered at lower levels and increased until the desirable therapeutic effect is achieved. The amount of lipid compound that is administered can vary and generally depends upon the amount of particular lipid compound and stabilizing material administered.

The present invention is further described in the following examples. In these examples, Examples 1 and 3 are actual examples. The remaining examples (Examples 2 and 4) are prophetic examples. These examples are for illustrative purposes only, and are not to be construed as limiting the appended claims.

EXAMPLES

Various of the materials used in the following examples are commercially available. Polylysine, alginic acid and chitosan were purchased from Sigma Chemical Co. (St. Louis, Mo.). Polyethyleneimine was purchased from Aldrich Chemical Co. (Milwaukee, Wis.).

In the following examples, "DPPE" refers to dipalmitoylphosphatidylethanolamine; "DPPA" refers to dipalmitolylphosphatidic acid; and "DPPC" refers to dipalmitoylphosphatidylcholine. "PEG 5000" refers to poly (ethylene glycol) polymer having a molecular weight of about 5000. "DPPE-PEG-5000" refers to DPPE which is covalently bound to PEG 5000.

EXAMPLE 1

This example describes the preparation and analysis of vesicular compositions within the scope of the present invention. The analysis involves a determination of the number and size of vesicles in the compositions.

Thirteen lipid compositions were prepared, each of which comprised a mixture of DPPE-PEG 5000 (62 mg), DPPA (9.2 mg) and DPPC (153.2 mg). Stock solutions (10 mg/mL) were formulated from stabilizing materials (polylysine, polyethyleneimine, alginic acid or chitosan) and deionized water. The stock solutions were added to twelve of the lipid compositions such that 7.6 mg (5 wt. %), 15.4 mg (10 wt. %) and 30.6 mg (20 wt. %) of each of the stabilizing materials were added to the lipid samples. No stabilizing material was added to the remaining lipid sample (control). Water was added to each of the lipid samples. The samples were stirred overnight and heated to about 45° C. for 1 to 2 hours and stirred again to achieve a homogeneous mixture. The mixtures were then cooled to 4° C. and lyophilized. Each of the lyophilizates (10 to 20 mg) was resuspended in a mixture of normal saline:propyleneglycol:glycerol (8:1:1, v:v:v) to a concentration of 1 mg/ml. The mixtures were heated to 45° C. and filtered (0.22 µm). Each of the resulting mixtures (1.5 mL) were placed in a 2 mL vial (1.1 mL gas headspace) (VWR, Los Angeles, Calif.). The vials were sealed and shaken on a Wig-L-Bug™ (Crescent Dental Lyons, Ill.) for 1 minute at a shaking rate of 3,300 rpm to provide gas-filled vesicles, the gas being air. Aliquots (20 µL) of each of the samples were removed and the vesicles were sized on an Accusizer Model 770 particle sizer (Particle Sizing Systems, Santa Barbara, Calif.).

The results of the analysis are set forth in the following table.

TABLE II

| Stabilizing Material | Weight % | Total Number of Vesicles | Vesicle Concentration (Number of Vesicles per mL) | Size (diam.) of Vesicles (µm) |
|---|---|---|---|---|
| None (Control) | 0 | N/S | N/S | N/S |
| Polylysine | 5 | $8.36 \times 10^4$ | $1.67 \times 10^6$ | 28.85 |
| | 10 | $9.34 \times 10^4$ | $1.87 \times 10^6$ | 26.47 |
| | 20 | $8.47 \times 10^4$ | $1.69 \times 10^6$ | 30.17 |
| Polyethyleneimine | 5 | $1.02 \times 10^5$ | $2.03 \times 10^6$ | 31.10 |
| | 10 | $8.14 \times 10^4$ | $1.63 \times 10^6$ | 30.29 |
| | 20 | $9.65 \times 10^4$ | $1.93 \times 10^6$ | 27.16 |
| Alginic Acid | 5 | $1.16 \times 10^5$ | $5.78 \times 10^6$ | 25.92 |
| | 10 | $1.08 \times 10^5$ | $5.65 \times 10^7$ | 28.12 |
| | 20 | $8.85 \times 10^4$ | $4.40 \times 10^7$ | 25.48 |
| Chitosan | 5 | $6.31 \times 10^4$ | $1.26 \times 10^6$ | 41.06 |
| | 10 | $6.95 \times 10^4$ | $1.39 \times 10^6$ | 32.19 |
| | 20 | $8.93 \times 10^4$ | $1.79 \times 10^6$ | 28.20 |

The foregoing results demonstrate that the compositions of the present invention, which comprise lipids in combination with a stabilizing material, possess high concentrations of vesicles relative to compositions lacking the stabilizing materials (control).

EXAMPLE 2(A)

This example demonstrates that bioactive agents, including, peptides, are effective as stabilizing materials.

The lipid compositions described in Example 1 will be prepared except that each of the stabilizing materials (polylysine, polyethyleneimine, alginic acid and chitosan) will be replaced with cystic fibrosis transmembrane receptor (CFTR). Gas-filled vesicles will be formed as described in Example 1. This demonstrates that CFTR acts as a stabilizing material.

The formulation containing CFTR will be injected intravenously (1 ml) to a patient suffering from cystic fibrosis. The symptoms of the patient are resolved after 4 weeks of therapy.

EXAMPLE 2(B)

Example 2(A) will be repeated except that vincristine (5 mg) will be substituted for the stabilizing materials described in Example 1. Gas-filled vesicles will be formed which demonstrates that the vincristine acts as a stabilizing material.

This composition will be used to treat a patient with a colon carcinoma status post-colonostomy but with metastasis to the liver. Tumor burden will be decreased with a minimum of adverse sequelae.

EXAMPLE 3

The viscosities of the compositions prepared in Example 1 were determined using a Brookfield Engineering Labs Viscometer with a CP42 Spindle. The spindle rotation rate was 1.1 sec$^{-1}$. The results are shown in the following table.

| Stabilizing Material | Weight % of Stabilizing Material (based on total lipid content) | Viscosity (mPas) |
|---|---|---|
| Control | 0 | 2.0 |
| Polylysine | 20 | 1.1 |
| Polyethyleneimine | 20 | 1.1 |
| Chitosan | 20 | 2.4 |
| Alginic Acid | 20 | 2.4 |

The results of the viscosity measurements tabulated above indicate that the stabilizing effect provided by the stabilizing materials is independent of viscosity. This is demonstrated, for example, in that the control composition, which contained no stabilizing material and in which substantially no gas-filled vesicles were formed, had a viscosity which is substantially similar to the viscosities of compositions that contained either alginic acid or chitosan and in which a desirable concentration of gas-filled vesicles was provided. In addition, the compositions which contained polylysine or polyethyleneimine as stabilizing material had a viscosity which was about one-half that of the control composition and the compositions which contained alginic acid and chitosan. As noted above, the compositions which contained polylysine and polyethyleneimine also provided desirable concentrations of gas-filled vesicles.

EXAMPLE 4

This example describes the use of stabilizing material which is covalently linked to a bioactive agent.

Into a 250 ml round-bottomed flask will be added nalidixic acid (5 g, 20 mmole) and alginic acid polymer (4.5 g, 20 mmole monomeric equivalents) having an average molecular weight of 240,000. The mixture will be dissolved in dimethylformamide (100 ml) and to this mixture will be added with stirring, carbonyldiimidazole (3.2 g, 20 mmole). The resulting mixture will be stirred for 1 hour and concentrated in vacuo. The resulting product will be passed through a gel size exclusion column to yield covalently-bound nalidixic acid alginate.

The lipid compositions of Example 1 will be prepared except that the stabilizing materials (polylysine, polyethyleneimine, alginic acid and chitosan) will be substituted with nalidixic acid alginate. Using the procedure described in Example 1, gas-filled vesicles will be prepared.

The compositions containing nalidixic acid alginate as a stabilizing material will be then injected intravenously (50 mL) to a patient with gram-negative bacteremia (pseudomonas aeruginosa). The bacteremia is resolved, presumably by the release in vivo of nalidixic acid from the nalidixic acid alginate due to cleavage with non-specific esterases in the bloodstream.

The disclosures of each patent, patent application and publication cited or described in this document are hereby incorporated by reference, in their entirety.

Various modifications of the invention, in addition to those described herein, will be apparent to those skilled in the art from the foregoing description. Such modifications are also intended to fall within the scope of the appended claims.

What is claimed is:

1. A vesicular composition comprising, in an aqueous carrier, vesicles comprising a lipid, a gas or gaseous precursor encapsulated in the vesicles, and a material which is capable of stabilizing the composition, wherein said stabilizing material is associated non-covalently with said lipid and is present in an amount sufficient to coat said lipid but insufficient to raise the viscosity of the composition, wherein said gas and gaseous precursor comprise a fluorinated compound selected from the group consisting of perfluorocarbons and sulfur hexafluoride, and wherein said stabilizing material comprises a polymer.

2. A composition according to claim 1 wherein said lipid comprises a phospholipid.

3. A composition according to claim 2 wherein said phospholipid is selected from the group consisting of phosphatidylcholine, phosphatidylethanolamine and phosphatidic acid.

4. A composition according to claim 3 wherein said phosphatidylcholine is selected from the group consisting of dioleoylphosphatidylcholine, dimyristoylphosphatidylcholine, dipalmitoylphosphatidylcholine and distearoylphosphatidylcholine.

5. A composition according to claim 4 wherein said phosphatidylcholine comprises dipalmitoylphosphatidylcholine.

6. A composition according to claim 3 wherein said phosphatidylethanolamine is selected from the group consisting of dipalmitoylphosphatidylethanolamine, dioleoylphosphatidylethanolamine, N-succinyldioleoylphosphatidylethanolamine and 1-hexadecyl-2-palmitoylglycerophosphoethanolamine.

7. A composition according to claim 6 wherein said phosphatidylethanolamine is dipalmitoylphosphatidylethanolamine.

8. A composition according to claim 3 wherein said phosphatidic acid comprises dipalmitolylphosphatidic acid.

9. A composition according to claim 1 wherein said polymer is selected from the group consisting of polyhydroxy, polyamine, polycarboxy and polysaccharide polymers.

10. A composition according to claim 1 which is selected from the group consisting of micelles and liposomes.

11. A composition according to claim 1 wherein said stabilizing material is present in an amount sufficient to lower the viscosity of the composition.

12. A composition according to claim 1 wherein said non-covalent association is selected from the group consisting of ionic interaction, dipole—dipole interaction and van der Waals forces.

13. A composition according to claim 1 further comprising a bioactive agent.

14. A vesicular composition according to claim 1 further comprising a polymer which is conjugated to at least a portion of said lipid.

15. A vesicular composition according to claim 14 wherein said polymer is selected from the group consisting of poly(ethylene glycol) (PEG), poly(vinylpyrrolidone), polyoxomers, polysorbate and polyvinyl alcohol.

16. A vesicular composition according to claim 15 wherein said PEG is selected from the group consisting of PEG 2,000, PEG 5,000 and PEG 8,000.

17. A vesicular composition according to claim 14 wherein said lipid-polymer conjugate is dipalmitoylphosphatidylethanolamine-PEG 5,000.

18. A formulation for therapeutic or diagnostic use comprising, in combination with a bioactive agent, vesicles comprising a lipid, a gas or gaseous precursor encapsulated in said vesicles, and a material which is capable of stabilizing the formulation, wherein said stabilizing material is associated non-covalently with said lipid and is present in an amount sufficient to coat said lipid but insufficient to raise the viscosity of the formulation, wherein said gas and gaseous precursor comprise a fluorinated compound selected from the group consisting of perfluorocarbons and sulfur hexafluoride, and wherein said stabilizing material comprises a polymer.

19. A formulation according to claim 18 wherein said vesicles are selected from the group consisting of micelles and liposomes.

20. A formulation according to claim 19 wherein said bioactive agent is substantially entrapped within said micelles or liposomes.

21. A process for the preparation of a stabilized vesicular composition comprising vesicles comprising a lipid, a gas or gaseous precursor encapsulated in the vesicles, and a stabilizing material which is capable of associating non-covalently with said lipid, wherein the process comprises combining together said lipid, gas or gaseous precursor, and stabilizing material, wherein said stabilizing material is combined with said lipid in an amount sufficient to coat said lipid but insufficient to raise the viscosity of the composition, wherein said gas and gaseous precursor comprise a fluorinated compound selected from the group consisting of perfluorocarbons and sulfur hexafluoride, and wherein said stabilizing material comprises a polymer.

22. A process according to claim 21 wherein said composition is selected from the group consisting of micelles and liposomes.

23. A process for the preparation of a formulation for diagnostic or therapeutic use comprising, in combination with a bioactive agent, a vesicular composition which comprises a lipid, a gas or gaseous precursor encapsulated in said vesicles, and a stabilizing material which is associated non-covalently with the lipid, wherein the process comprises combining together said bioactive agent and vesicular composition, wherein said stabilizing material is present in said composition in an amount sufficient to coat said lipid but insufficient to raise the viscosity of said composition, wherein said gas and gaseous precursor comprise a fluorinated compound selected from the group consisting of perfluorocarbons and sulfur hexafluoride, and wherein said stabilizing material comprises a polymer.

24. A process according to claim 23 wherein said composition is selected from the group consisting of micelles and liposomes.

25. A stabilized vesicular composition comprising a lipid, a gas or gaseous precursor encapsulated in the vesicles, and a stabilizing material which is capable of associating non-covalently with said lipid, wherein the composition is prepared by combining together said lipid, gas or gaseous precursor, and stabilizing material, wherein said stabilizing material is combined with said lipid in an amount sufficient to coat said lipid but insufficient to raise the viscosity of the composition, wherein said gas and gaseous precursor comprise a fluorinated compound selected from the group consisting of perfluorocarbons and sulfur hexafluoride, and wherein said stabilizing material comprises a polymer.

26. A stabilized formulation for diagnostic or therapeutic use comprising a bioactive agent and a vesicular composition which comprises a lipid, a gas or gaseous precursor encapsulated in said vesicles, and a material which is capable of stabilizing the formulation and is associated non-covalently with said lipid, wherein said composition is prepared by combining together said lipid, gas or gaseous precursor and stabilizing material, wherein said stabilizing material is present in an amount sufficient to coat said lipid but insufficient to raise the viscosity of the formulation, wherein said gas and gaseous precursor comprise a fluorinated compound selected from the group consisting of perfluorocarbons and sulfur hexafluoride, and wherein said stabilizing material comprises a polymer.

27. A method for providing an image of an internal region of a patient comprising (i) administering to the patient a vesicular composition comprising, in an aqueous carrier, vesicles comprising a lipid, a gas or a gaseous precursor encapsulated in said vesicles, and a material which is capable of stabilizing the composition, wherein said stabilizing material is associated non-covalently with said lipid and is present in an amount sufficient to coat said lipid but insufficient to raise the viscosity of the composition, wherein said gas and gaseous precursor comprise a fluorinated compound selected from the group consisting of perfluorocarbons and sulfur hexafluoride, and wherein said stabilizing material comprises a polymer; and (ii) scanning the patient using ultrasound to obtain a visible image of the region.

28. A method for diagnosing the presence of diseased tissue in a patient comprising (i) administering to the patient a vesicular composition comprising, in an aqueous carrier, vesicles comprising a lipid, a gas or a gaseous precursor encapsulated in said vesicles, and a material which is capable of stabilizing the composition, wherein said stabilizing material is associated non-covalently with said lipid and is present in an amount sufficient to coat said lipid but insufficient to raise the viscosity of the composition, wherein said gas and gaseous precursor comprise a fluorinated compound selected from the group consisting of perfluorocarbons and sulfur hexafluoride, and wherein said stabilizing material comprises a polymer; and (ii) scanning the patient using ultrasound to obtain a visible image of any diseased tissue in the patient.

29. A method for the therapeutic delivery in vivo of a bioactive agent comprising administering to a patient a therapeutically effective amount of a formulation which comprises, in combination with a bioactive agent, a vesicular composition comprising a lipid, a gas or gaseous precursor encapsulated in said vesicles, and a material which stabilizes said composition, wherein said stabilizing material is associated noncovalently with said lipid and is present in said composition in an amount sufficient to coat said lipid but insufficient to raise the viscosity of said composition, wherein said said gas and gaseous precursor comprise a fluorinated compound selected from the group consisting of perfluorocarbons and sulfur hexafluoride, and wherein said stabilizing material comprises a polymer.

30. A composition according to claim 1 wherein said fluorinated compound is sulfur hexafluoride.

31. A composition according to claim 1 wherein said fluorinated compound comprises a perfluorocarbon.

32. A composition according to claim 1 wherein said vesicles are selected from the group consisting of unilamellar, oligolamellar and multilamellar vesicles.

33. A composition according to claim 32 wherein said vesicles comprise unilamellar vesicles.

34. A composition according to claim 33 wherein said vesicles comprise a monolayer.

35. A composition according to claim 34 wherein said lipid is a phospholipid and said fluorinated compound is perfluoropentane.

36. A composition according to claim 34 wherein said lipid is a phospholipid and said fluorinated compound is perfluoropropane.

37. A composition according to claim 34 wherein said lipid is a phospholipid and said fluorinated compound is sulfur hexafluoride.

38. A composition according to claim 33 wherein said vesicles comprise a bilayer.

39. A composition according to claim 38 wherein said lipid is a phospholipid and said fluorinated compound is perfluoropentane.

40. A composition according to claim 38 wherein said lipid is a phospholipid and said fluorinated compound is perfluoropropane.

41. A composition according to claim 38 whereto said lipid is a phospholipid and said fluorinated compound is sulfur hexafluoride.

42. A composition according to claim 32 wherein said vesicles are selected from the group consisting of oligolamellar and multilamellar vesicles.

43. A composition according to claim 42 wherein said vesicles comprise a monolayer.

44. A composition according to claim 43 wherein said lipid is a phospholipid and said fluorinated compound is perfluoropentane.

45. A composition according to claim 43 whereto said lipid is a phospholipid and said fluorinated compound is perfluoropropane.

46. A composition according to claim 43 wherein said lipid is a phospholipid and said fluorinated compound is sulfur hexafluoride.

47. A composition according to claim 42 wherein said vesicles comprise a bilayer.

48. A composition according to claim 47 wherein said lipid is a phospholipid and said fluorinated compound is perfluoropentane.

49. A composition according to claim 47 wherein said lipid is a phospholipid and said fluorinated compound is perfluoropropane.

50. A composition according to claim 47 wherein said lipid is a phospholipid and said fluorinated compound is sulfur hexafluoride.

51. A formulation according to claim 18 wherein said fluorinated compound is sulfur hexafluoride.

52. A formulation according to claim 18 wherein said fluorinated compound comprises a perfluorocarbon.

53. A formulation according to claim 18 wherein said vesicles are selected from the group consisting of unilamellar, oligolamellar and multilamellar vesicles.

54. A formulation according to claim 53 wherein said vesicles comprise unilamellar vesicles.

55. A formulation according to claim 54 wherein said vesicles comprise a monolayer.

56. A formulation according to claim 55 wherein said lipid is a phospholipid and said fluorinated compound is perfluoropentane.

57. A formulation according to claim 55 wherein said lipid is a phospholipid and said fluorinated compound is perfluoropropane.

58. A formulation according to claim 55 wherein said lipid is a phospholipid and said fluorinated compound is sulfur hexafluoride.

59. A formulation according to claim 54 wherein said vesicles comprise a bilayer.

60. A formulation according to claim 59 wherein said lipid is a phospholipid and said fluorinated compound is perfluoropentane.

61. A formulation according to claim 59 wherein said lipid is a phospholipid and said fluorinated compound is perfluoropropane.

62. A formulation according to claim 59 wherein said lipid is a phospholipid and said fluorinated compound is sulfur hexafluoride.

63. A formulation according to claim 53 whereto said vesicles are selected from the group consisting of oligolamellar and multilamellar vesicles.

64. A formulation according to claim 63 wherein said vesicles comprise a monolayer.

65. A formulation according to claim 64 wherein said lipid is a phospholipid and said fluorinated compound is perfluoropentane.

66. A formulation according to claim 64 wherein said lipid is a phospholipid and said fluorinated compound is perfluoropropane.

67. A formulation according to claim 64 wherein said lipid is a phospholipid and said fluorinated compound is sulfur hexafluoride.

68. A formulation according to claim 63 wherein said vesicles comprise a bilayer.

69. A formulation according to claim 68 wherein said lipid is a phospholipid and said fluorinated compound is perfluoropentane.

70. A formulation according to claim 68 wherein said lipid is a phospholipid and said fluorinated compound is perfluoropropane.

71. A formulation according to claim 68 wherein said lipid is a phospholipid and said fluorinated compound is sulfur hexafluoride.

72. A process according to claim 21 wherein said fluorinated compound is sulfur hexafluoride.

73. A process according to claim 21 wherein said fluorinated compound comprises a perfluorocarbon.

74. A process according to claim 21 wherein said vesicles are selected from the group consisting of unilamellar, oligolamellar and multilamellar vesicles.

75. A process according to claim 74 wherein said vesicles comprise unilamellar vesicles.

76. A process according to claim 75 wherein said vesicles comprise a monolayer.

77. A process according to claim 76 wherein said lipid is a phospholipid and said fluorinated compound is perfluoropentane.

78. A process according to claim 76 wherein said lipid is a phospholipid and said fluorinated compound is perfluoropropane.

79. A process according to claim 76 wherein said lipid is a phospholipid and said fluorinated compound is sulfur hexafluoride.

80. A process according to claim 75 wherein said vesicles comprise a bilayer.

81. A process according to claim 80 wherein said lipid is a phospholipid and said fluorinated compound is perfluoropentane.

82. A process according to claim 80 wherein said lipid is a phospholipid and said fluorinated compound is perfluoropropane.

83. A process according to claim 80 wherein said lipid is a phospholipid and said fluorinated compound is sulfur hexafluoride.

84. A process according to claim 74 wherein said vesicles are selected from the group consisting of oligolamellar and multilamellar vesicles.

85. A process according to claim 84 wherein said vesicles comprise a monolayer.

86. A process according to claim 85 wherein said lipid is a phospholipid and said fluorinated compound is perfluoropentane.

87. A process according to claim 85 wherein said lipid is a phospholipid and said fluorinated compound is perfluoropropane.

88. A process according to claim 85 wherein said lipid is a phospholipid and said fluorinated compound is sulfur hexafluoride.

89. A process according to claim 84 wherein said vesicles comprise a bilayer.

90. A process according to claim 89 wherein said lipid is a phospholipid and said fluorinated compound is perfluoropentane.

91. A process according to claim 89 wherein said lipid is a phospholipid and said fluorinated compound is perfluoropropane.

92. A process according to claim 89 wherein said lipid is a phospholipid and said fluorinated compound is sulfur hexafluoride.

93. A process according to claim 23 whereto said fluorinated compound is sulfur hexafluoride.

94. A process according to claim 23 wherein said fluorinated compound comprises a perfluorocarbon.

95. A process according to claim 23 wherein said vesicles are selected from the group consisting of unilamellar, oligolamellar and multilamellar vesicles.

96. A process according to claim 95 wherein said vesicles comprise unilamellar vesicles.

97. A process according to claim 95 wherein said vesicles comprise a monolayer.

98. A process according to claim 97 wherein said lipid is a phospholipid and said fluorinated compound is perfluoropentane.

99. A process according to claim 97 wherein said lipid is a phospholipid and said fluorinated compound is perfluoropropane.

100. A process according to claim 97 wherein said lipid is a phospholipid and said fluorinated compound is sulfur hexafluoride.

101. A process according to claim 96 wherein said vesicles comprise a bilayer.

102. A process according to claim 101 wherein said lipid is a phospholipid and said fluorinated compound is perfluoropentane.

103. A process according to claim 101 wherein said lipid is a phospholipid and said fluorinated compound is perfluoropropane.

104. A process according to claim 101 wherein said lipid is a phospholipid and said fluorinated compound is sulfur hexafluoride.

105. A process according to claim 95 wherein said vesicles are selected from the group consisting of oligolamellar and multilamellar vesicles.

106. A process according to claim 105 wherein said vesicles comprise a monolayer.

107. A process according to claim 106 wherein said lipid is a phospholipid and said fluorinated compound is perfluoropentane.

108. A process according to claim 106 wherein said lipid is a phospholipid and said fluorinated compound is perfluoropropane.

109. A process according to claim 106 wherein said lipid is a phospholipid and said fluorinated compound is sulfur hexafluoride.

110. A process according to claim 105 wherein said vesicles comprise a bilayer.

111. A process according to claim 110 wherein said lipid is a phospholipid and said fluorinated compound is perfluoropentane.

112. A process according to claim 110 wherein said lipid is a phospholipid and said fluorinated compound is perfluoropropane.

113. A process according to claim 110 wherein said lipid is a phospholipid and said fluorinated compound is sulfur hexafluoride.

114. A composition according to claim 25 wherein said fluorinated compound is sulfur hexafluoride.

115. A composition according to claim 25 wherein said fluorinated compound comprises a perfluorocarbon.

116. A composition according to claim 25 wherein said vesicles are selected from the group consisting of unilamellar, oligolamellar and multilamellar vesicles.

117. A composition according to claim 116 wherein said vesicles comprise unilamellar vesicles.

118. A composition according to claim 117 wherein said vesicles comprise a monolayer.

119. A composition according to claim 118 wherein said lipid is a phospholipid and said fluorinated compound is perfluoropentane.

120. A composition according to claim 118 wherein said lipid is a phospholipid and said fluorinated compound is perfluoropropane.

121. A composition according to claim 118 wherein said lipid is a phospholipid and said fluorinated compound is sulfur hexafluoride.

122. A composition according to claim 117 wherein said vesicles comprise a bilayer.

123. A composition according to claim 122 wherein said lipid is a phospholipid and said fluorinated compound is perfluoropentane.

124. A composition according to claim 122 wherein said lipid is a phospholipid and said fluorinated compound is perfluoropropane.

125. A composition according to claim 122 wherein said lipid is a phospholipid and said fluorinated compound is sulfur hexafluoride.

126. A composition according to claim 116 wherein said vesicles are selected from the group consisting of oligolamellar and multilamellar vesicles.

127. A composition according to claim 126 wherein said vesicles comprise a monolayer.

128. A composition according to claim 126 wherein said lipid is a phospholipid and said fluorinated compound is perfluoropentane.

129. A composition according to claim 126 wherein said lipid is a phospholipid and said fluorinated compound is perfluoropropane.

130. A composition according to claim 126 wherein said lipid is a phospholipid and said fluorinated compound is sulfur hexafluoride.

131. A composition according to claim 126 wherein said vesicles comprise a bilayer.

132. A composition according to claim 131 wherein said lipid is a phospholipid and said fluorinated compound is perfluoropentane.

133. A composition according to claim 131 wherein said lipid is a phospholipid and said fluorinated compound is perfluoropropane.

134. A composition according to claim 131 wherein said lipid is a phospholipid and said fluorinated compound is sulfur hexafluoride.

135. A formulation according to claim 26 wherein said fluorinated compound is sulfur hexafluoride.

136. A formulation according to claim 26 wherein said fluorinated compound comprises a perfluorocarbon.

137. A formulation according to claim 26 wherein said vesicles are selected from the group consisting of unilamellar, oligolamellar and multilamellar vesicles.

138. A formulation according to claim 137 wherein said vesicles comprise unilamellar vesicles.

139. A formulation according to claim 138 wherein said vesicles comprise a monolayer.

140. A formulation according to claim 138 wherein said lipid is a phospholipid and said fluorinated compound is perfluoropentane.

141. A formulation according to claim 138 wherein said lipid is a phospholipid and said fluorinated compound is perfluoropropane.

142. A formulation according to claim 138 wherein said lipid is a phospholipid and said fluorinated compound is sulfur hexafluoride.

143. A formulation according to claim 137 wherein said vesicles comprise a bilayer.

144. A formulation according to claim 143 wherein said lipid is a phospholipid and said fluorinated compound is perfluoropentane.

145. A formulation according to claim 143 wherein said lipid is a phospholipid and said fluorinated compound is perfluoropropane.

146. A formulation according to claim 143 wherein said lipid is a phospholipid and said fluorinated compound is sulfur hexafluoride.

147. A formulation according to claim 137 wherein said vesicles are selected from the group consisting of oligolamellar and multilamellar vesicles.

148. A formulation according to claim 147 wherein said vesicles comprise a monolayer.

149. A formulation according to claim 148 wherein said lipid is a phospholipid and said fluorinated compound is perfluoropentane.

150. A formulation according to claim 148 wherein said lipid is a phospholipid and said fluorinated compound is perfluoropropane.

151. A formulation according to claim 148 wherein said lipid is a phospholipid and said fluorinated compound is sulfur hexafluoride.

152. A formulation according to claim 14 wherein said vesicles comprise a bilayer.

153. A formulation according to claim 152 wherein said lipid is a phospholipid and said fluorinated compound is perfluoropentane.

154. A formulation according to claim 152 wherein said lipid is a phospholipid and said fluorinated compound is perfluoropropane.

155. A formulation according to claim 152 wherein said lipid is a phospholipid and said fluorinated compound is sulfur hexafluoride.

156. A method according to claim 27 wherein said fluorinated compound is sulfur hexafluoride.

157. A method according to claim 27 wherein said fluorinated compound comprises a perfluorocarbon.

158. A method according to claim 27 wherein said vesicles are selected from the group consisting of unilamellar, oligolamellar and multilamellar vesicles.

159. A method according to claim 158 wherein said vesicles comprise unilamellar vesicles.

160. A method according to claim 159 wherein said vesicles comprise a monolayer.

161. A method according to claim 160 wherein said lipid is a phospholipid and said fluorinated compound is perfluoropentane.

162. A method according to claim 160 wherein said lipid is a phospholipid and said fluorinated compound is perfluoropropane.

163. A method according to claim 160 wherein said lipid is a phospholipid and said fluorinated compound is sulfur hexafluoride.

164. A method according to claim 159 wherein said vesicles comprise a bilayer.

165. A method according to claim 164 wherein said lipid is a phospholipid and said fluorinated compound is perfluoropentane.

166. A method according to claim 164 wherein said lipid is a phospholipid and fluorinated compound is perfluoropropane.

167. A method according to claim 164 wherein said lipid is a phospholipid and said fluorinated compound is sulfur hexafluoride.

168. A method according to claim 158 wherein said vesicles are selected from the group consisting of oligolamellar and multilamellar vesicles.

169. A method according to claim 168 wherein said vesicles comprise a monolayer.

170. A method according to claim 169 wherein said lipid is a phospholipid and said fluorinated compound is perfluoropentane.

171. A method according to claim 169 wherein said lipid is a phospholipid and said fluorinated compound is perfluoropropane.

172. A method according to claim 169 wherein said lipid is a phospholipid and said fluorinated compound is sulfur hexafluoride.

173. A method according to claim 168 wherein said vesicles comprise a bilayer.

174. A method according to claim 173 wherein said lipid is a phospholipid and said fluorinated compound is perfluoropentane.

175. A method according to claim 173 wherein said lipid is a phospholipid and said fluorinated compound is perfluoropropane.

176. A method according to claim 173 wherein said lipid is a phospholipid and said fluorinated compound is sulfur hexafluoride.

177. A method according to claim 28 wherein said fluorinated compound is sulfur hexafluoride.

178. A method according to claim 28 wherein said fluorinated compound comprises a perfluorocarbon.

179. A method according to claim 28 wherein said vesicles are selected from the group consisting of unilamellar, oligolamellar and multilamellar vesicles.

180. A method according to claim 179 wherein said vesicles comprise unilamellar vesicles.

181. A method according to claim 180 wherein said vesicles comprise a monolayer.

182. A method according to claim 181 wherein said lipid is a phospholipid and said fluorinated compound is perfluoropentane.

183. A method according to claim 181 wherein said lipid is a phospholipid and said fluorinated compound is perfluoropropane.

184. A method according to claim 181 wherein said lipid is a phospholipid and said fluorinated compound is sulfur hexafluoride.

185. A method according to claim 180 wherein said vesicles comprise a bilayer.

186. A method according to claim 185 wherein said lipid is a phospholipid and said fluorinated compound is perfluoropentane.

187. A method according to claim 185 wherein said lipid is a phospholipid and said fluorinated compound is perfluoropropane.

188. A method according to claim 185 wherein said lipid is a phospholipid and said fluorinated compound is sulfur hexafluoride.

189. A method according to claim 179 wherein said vesicles are selected from the group consisting of oligolamellar and multilamellar vesicles.

190. A method according to claim 189 wherein said vesicles comprise a monolayer.

191. A method according to claim 190 wherein said lipid is a phospholipid and said fluorinated compound is perfluoropentane.

192. A method according to claim 190 wherein said lipid is a phospholipid and said fluorinated compound is perfluoropropane.

193. A method according to claim 190 wherein said lipid is a phospholipid and said fluorinated compound is sulfur hexafluoride.

194. A method according to claim 189 wherein said vesicles comprise a bilayer.

195. A method according to claim 194 wherein said lipid is a phospholipid and said fluorinated compound is perfluoropentane.

196. A method according to claim 194 wherein said lipid is a phospholipid and said fluorinated compound is perfluoropropane.

197. A method according to claim 194 wherein said lipid is a phospholipid and said fluorinated compound is sulfur hexafluoride.

198. A method according to claim 29 wherein said fluorinated compound is sulfur hexafluoride.

199. A method according to claim 29 wherein said fluorinated compound comprises a perfluorocarbon.

200. A method according to claim 29 wherein said vesicles are selected from the group consisting of unilamellar, oligolamellar and multilamellar vesicles.

201. A method according to claim 200 wherein said vesicles comprise unilamellar vesicles.

202. A method according to claim 201 wherein said vesicles comprise a monolayer.

203. A method according to claim 202 wherein said lipid is a phospholipid and said fluorinated compound is perfluoropentane.

204. A method according to claim 202 wherein said lipid is a phospholipid and said fluorinated compound is perfluoropropane.

205. A method according to claim 202 wherein said lipid is a phospholipid and said fluorinated compound is sulfur hexafluoride.

206. A method according to claim 201 wherein said vesicles comprise a bilayer.

207. A method according to claim 206 wherein said lipid is a phospholipid and said fluorinated compound is perfluoropentane.

208. A method according to claim 206 wherein said lipid is a phospholipid and said fluorinated compound is perfluoropropane.

209. A method according to claim 206 wherein said lipid is a phospholipid and said fluorinated compound is sulfur hexafluoride.

210. A method according to claim 200 wherein said vesicles are selected from the group consisting of oligolamellar and multilamellar vesicles.

211. A method according to claim 210 wherein said vesicles comprise a monolayer.

212. A method according to claim 211 wherein said lipid is a phospholipid and said fluorinated compound is perfluoropentane.

213. A method according to claim 211 wherein said lipid is a phospholipid and said fluorinated compound is perfluoropropane.

214. A method according to claim 211 wherein said lipid is a phospholipid and said fluorinated compound is sulfur hexafluoride.

215. A method according to claim 210 wherein said vesicles comprise a bilayer.

216. A method according to claim 215 wherein said lipid is a phospholipid and said fluorinated compound is perfluoropentane.

217. A method according to claim 215 wherein said lipid is a phospholipid and said fluorinated compound is perfluoropropane.

218. A method according to claim 215 wherein said lipid is a phospholipid and said fluorinated compound is sulfur hexafluoride.

219. A composition according to claim 31 wherein said perfluorocarbon is selected from the group consisting of perfluoromethane, perfluoroethane, perfluoropropane, perfluorobutane and perfluorocyclobutane.

220. A formulation according to claim 18 wherein said perfluorocarbon is selected from the group consisting of perfluoromethane, perfluoroethane, perfluoropropane, perfluorobutane and perfluorocyclobutane.

\* \* \* \* \*

UNITED STATES PATENT AND TRADEMARK OFFICE
CERTIFICATE OF CORRECTION

PATENT NO. : 5,705,187
DATED : Jan. 6, 1998
INVENTOR(S) : Unger

It is certified that error appears in the above-identified patent and that said Letters Patent is hereby corrected as shown below:

On the title page:

In the "Related U.S. Application Data" section, third line from the bottom of section [63], after "717,084,", please insert --, Jun. 18, 1991, Pat. No. 5,228,446,--.

In the "Related U.S. Application Data" section, second line from the bottom of section [63], after "899," please insert --Jun. 18, 1991, abandoned,--.

In the "Related U.S. Application Data" section, second line from the bottom of section [63], after "Ser. No. 569,828,", please insert --Aug. 20, 1990, Pat. No. 5,088,499,--.

In the "Related U.S. Application Data" section, last line of section [63], after "455,707" please insert --Dec. 22, 1989, abandoned.--.

In the "References Cited", "U.S. PATENT DOCUMENTS" section, at "4,569,836", after "Gordon", please insert --...............424/1.1--.

On page 2, first column, in the "References Cited", "U.S. PATENT DOCUMENTS" section, at "5,305,757", please delete "Under et al." and insert --Unger et al.-- therefor.

On page 3, first column, in the "References Cited", "OTHER PUBLICATIONS" section, at "Keller et al.,", please delete "Opacitication" and insert --Opacification-- therefor.

UNITED STATES PATENT AND TRADEMARK OFFICE
CERTIFICATE OF CORRECTION

PATENT NO. : 5,705,187
DATED : Jan. 6, 1998
INVENTOR(S) : Unger

It is certified that error appears in the above-identified patent and that said Letters Patent is hereby corrected as shown below:

On page 3, first column, in the "References Cited", "OTHER PUBLICATIONS" section, at "Tilcock et al.,", second line thereof, please delete "pp. 70-80" and insert --pp. 77-80-- therefor.

On page 4, first column, in the "References Cited", "OTHER PUBLICATIONS" section, at "Poznansky et al.,", second line thereof, please delete "Biologica" and insert --Biological-- therefor.

On page 4, second column, in the "References Cited", "OTHER PUBLICATIONS" section, at "El-Gorab,", third line thereof, please delete "*Acta*, 306," and insert --*Acta*, 1973, 306,-- therefor.

In column 1, line 10, after "5,585,112," please insert --issued Dec. 17, 1996,--.

In column 1, line 31, after "5,580,575," please insert --issued Dec. 3, 1996,--.

In column 1, line 39, please insert, as a new paragraph, --The disclosures of each of the above applications are incorporated herein by reference in their entirety.--.

In column 9, line 6, please delete "metheylammonium" and insert --methylammonium-- therefor.

UNITED STATES PATENT AND TRADEMARK OFFICE
CERTIFICATE OF CORRECTION

PATENT NO. : 5,705,187
DATED : Jan. 6, 1998
INVENTOR(S) : Unger

It is certified that error appears in the above-identified patent and that said Letters Patent is hereby corrected as shown below:

In column 10, line 20, please delete "1'10$^9$" and insert --1 x 10$^9$-- therefor.

In column 14, line 9, please delete "carded" and insert --carried-- therefor.

In column 17, line 62, please delete "to bound" and insert --to be bound-- therefor.

In column 20, line 4, please delete "Wain" and insert --train-- therefor.

In column 20, line 12, please delete "5.0 W/cm:," and insert --5.0 W/cm$^2$,-- therefor.

In column 20, line 13, please delete "2.5 W/cm:" and insert --2.5 W/cm$^2$-- therefor.

In column 21, line 32, please delete "Crescent Dental" and insert --Crescent Dental,-- therefor.

In column 21, line 58, after "TABLE II", please insert --"N/S" means not significant--.

In column 26, claim 29, line 2, please delete "wherein said said gas" and insert --wherein said gas-- therefor.

In column 26, claim 41, line 33, please delete "whereto" and insert --wherein-- therefor.

UNITED STATES PATENT AND TRADEMARK OFFICE
CERTIFICATE OF CORRECTION

PATENT NO. : 5,705,187
DATED : Jan. 6, 1998
INVENTOR(S) : Unger

It is certified that error appears in the above-identified patent and that said Letters Patent is hereby corrected as shown below:

In column 26, claim 45, line 44, please delete "whereto" and insert --wherein-- therefor.

In column 27, claim 63, line 24, please delete "whereto" and insert --wherein-- therefor.

In column 28, claim 93, line 37, please delete "whereto" and insert --wherein-- therefor.

In column 28, claim 97, please delete "claim 95" and insert --claim 96-- therefor.

In column 31, claim 166, line 29, please delete "and fluorinated" and insert --and said fluorinated-- therefor.

Signed and Sealed this

Twenty-sixth Day of October, 1999

Attest:

Q. TODD DICKINSON

Attesting Officer

Acting Commissioner of Patents and Trademarks